United States Patent
Jarrott et al.

(10) Patent No.: US 6,232,314 B1
(45) Date of Patent: May 15, 2001

(54) ARYLALKYLPIPERAZINE COMPOUNDS AS ANTIOXIDANTS

(75) Inventors: Bevyn Jarrott, Donvale; Philip Mark Beart, Ivanhoe; William Roy Jackson, Burwood; Vijaya Bhaskar Kenche, Clayton North; Alan Duncan Robertson, South Melbourne; Maree Patricia Collis, Prahran, all of (AU)

(73) Assignee: Monash University, Victoria (AU)

( * ) Notice: Subject to any disclaimer, the term of this patent is extended or adjusted under 35 U.S.C. 154(b) by 0 days.

(21) Appl. No.: 09/180,258

(22) PCT Filed: May 12, 1997

(86) PCT No.: PCT/AU97/00293

§ 371 Date: Mar. 18, 1999

§ 102(e) Date: Mar. 18, 1999

(87) PCT Pub. No.: WO97/43259

PCT Pub. Date: Nov. 20, 1997

(30) Foreign Application Priority Data

May 10, 1996 (AU) .............................................. 9772

(51) Int. Cl.$^7$ ................... C07D 295/092; C07D 401/06; A61K 31/4965; A61K 31/497; A61P 25/18

(52) U.S. Cl. ................... 514/252.12; 544/360; 544/363; 544/369; 544/373; 544/376; 544/377; 544/392; 544/401; 514/252.13; 514/253.01; 514/253.06; 514/254.02; 514/254.09; 514/254.11; 514/255.03

(58) Field of Search .................... 544/391, 401, 544/376, 377, 360, 369, 363, 373, 392, 379; 514/252.12, 252.13, 254.02, 254.09, 254.11

(56) References Cited

U.S. PATENT DOCUMENTS

| | | | |
|---|---|---|---|
| 3,505,334 | * 4/1970 | Regnier et al. ..................... | 260/268 |
| 3,959,283 | 5/1976 | Lafon ................................... | 260/265 |
| 4,127,661 | 11/1978 | Falconnet et al. .................. | 424/250 |

FOREIGN PATENT DOCUMENTS

| | | |
|---|---|---|
| 2344681 | * 3/1974 | (DE) . |
| 0 404 197 A2 | 12/1990 | (EP) . |
| 2 474 031 | 7/1981 | (FR) . |
| 3-173853 A2 | * 7/1991 | (JP) . |

OTHER PUBLICATIONS

Wiley, J.L., Exp. Clin. Psychopharmacol., 5(4), 1997, 365–374; cited in Medline PMID:9386963.*
Luigi et al., Chem. Abstract, 81: 3968 (1974).*
Chikara et al., Chem. Abstract, 115: 279593 (1991).*
Patent Abstract of Japan vol. 6, No. 227, Dec. 11, 1982.
Hiroshi, Ohtaka et al., "Benzylpiperazine Derivatives. II. Syntheses and Cerebral Vasodilating Activities of 1–[(3–Alkyl–3–hydroxy–3–phenyl) propyl]–4–benzylpiperazine Derivatives", Chem. Pharm. Bull., vol. 35: 2782–2791 (1987).
Hiroshi, Ohtaka et al., "Benzylpiperazine Derivatives. III. Quantitative Structure–Cerebral Vasodilating Activity Relationships of 1–Benzyl–7–(3–hydroxy–3–phenylpentyl)-piperazine Derivatives", Chem. Pharm. Bull., vol. 35: 2732–2796 (1987).

* cited by examiner

Primary Examiner—Richard L. Raymond
Assistant Examiner—Thomas McKenzie
(74) Attorney, Agent, or Firm—Scully, Scott, Murphy & Presser

(57) ABSTRACT

Arylalkylpiperazine compounds (1) wherein B is aryl or optionally substituted aryl; $R_1$ is hydroxy; $R_2$ and $R_3$ are the same or different and are independently selected from hydrogen or $C_{1-3}$ alkyl; m is 0, 1 or 2; D is a linking chain of atoms which may be optionally substituted and which contains from 1 to 8 atoms in the chain; E is a phenolic antioxidant group or a corresponding amino derivative thereof wherein the phenolic hydroxyl is replaced by amino, are disclosed. The compounds have both free radical scavenging activity and block excitatory amino acid activity. Some compounds of the present invention also display an affinity for voltage-sensitive sodium channels.

29 Claims, No Drawings

ARYLALKYLPIPERAZINE COMPOUNDS AS ANTIOXIDANTS

The present invention relates to arylalkylpiperazine compounds, methods for their manufacture, pharmaceutical formulations of such compounds and their use in therapy, particularly in the treatment of disorders related to neurological damage of the central nervous system.

Damage to the neurones of the central nervous system may result from acute events that lead to ischaemia or other forms of hypoxia, or from neurodegenerative diseases such as Alzheimer's disease, Parkinson's disease, Huntington's disease or lateral amyotrophic sclerosis. The mechanism of such neuronal injury is complex, however, extensive investigation of such processes has identified the over stimulation of receptors for excitatory amino acids, for example L-glutamate, and oxidative processes as playing a role in the pathway to neurodegeneration resulting from both acute ischaemic or anoxic events and a wide variety of chronic neurological disorders (Coyle et al., 1993; and Lipton et al., 1994). These two mechanisms are not totally independent, part of the cascade of events that follow over stimulation of receptors for excitatory amino acids has been shown to be an effective increase in the generation of reactive free radicals. Recent evidence also indicates that two cytodestructive events may be involved in excitotoxic/free radical-induced cell death—necrosis and apoptosis (Bonfocco et al., 1995). The latter event, also termed programmed cell death, is considered to occur in normal development and in the aging process.

Glutamate is the major excitatory neurotransmitter present in the brain and spinal cord, and glutamate receptors are divided into two main subtypes, ionotropic and metabotropic. A particular ionotropic glutamate receptor identified as being involved in excitatory amino acid induced neuronal damage in the brain and central nervous system is the N-methyl-D-aspartate (NMDA) receptor complex (Meldrum et al., 1989; and Choi, 1992). This receptor-ionophore complex has a number of modulatory sites associated with it, including the glycine site, the NMDA or glutamate site, the channel, the polyamine site, a pH sensitive region, a redox site, and a zinc-binding site. Compounds that block the activity of the NMDA receptor complex by binding to these various sites and by preventing subsequent entry of $Ca^{2+}$ have been indicated as neuroprotective agents. For example, ifenprodil and eliprodil have been reported as interacting with the polyamine sensitive binding site of the NMDA receptor (Carter et al., 1989 and 1990; Reynolds et al., 1989; Robinson et al., 1990; Beart et al., 1995) and have been reported as having neuroprotective properties in models of neurodegeneration following ischaemia (Gotti et al., 1988). Similarly, compounds that modulate voltage-sensitive sodium channels may also inhibit release of excitatory amino acids and may be useful in neuronal protection (Lysko et al., 1995 and Urenjak et al., 1996).

The present invention is directed to the provision of new compounds that have both free radical scavenging activity and block excitatory amino acid activity, preferably at the NMDA receptor complex via its polyamine site.

Some compounds of the present invention also display an affinity for voltage-sensitive sodium channels.

Accordingly in a first aspect, the present invention provides arylalkylpiperazine compounds of formula (1)

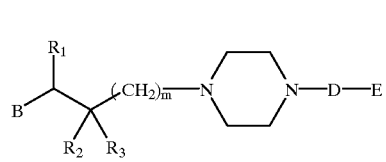

wherein
B is aryl or optionally substituted aryl;
$R^1$ is hydroxy;
$R^2$ and $R^3$ are the same or different and are independently selected from hydrogen or $C_{1-3}$ alkyl;
m is 0, 1 or 2. Preferably m is 0 or 1;
D is a linking chain of atoms which may be optionally substituted and contains from 1–8 atoms in the chain, and wherein preferably the atoms of the chain are carbon, oxygen, nitrogen or sulfur, more preferably the atoms of the chain are carbon atoms present either as a carbonyl, a straight chain or branched alkyl, oxoalkyl, alkenyl or oxoalkenyl group of 1–6 carbons; examples of D include $(CH_2)_n$, $C(=O)(CH_2)_{n-1}$, $C(=O)CH=CH$ or $(CH_2)_nCH=CH$ wherein n is 1–6
E is a phenolic antioxidant group or a corresponding amino derivative thereof, wherein the phenolic hydroxyl is replaced by amino, with antioxidant properties; and salts thereof, solvates thereof, pharmaceutically acceptable derivatives thereof, prodrugs thereof, tautomers thereof and/or isomers thereof.

In this specification "aryl" used either alone or in compound words such as "aryloxy", "arylthio", "arylamino" or "diarylamino" denotes single, polynuclear, conjugated and fused residues of aromatic hydrocarbons or aromatic heterocyclic ring systems. Examples of aryl include but are not limited to phenyl, naphthyl, fluorenyl, pyrenyl, pyridyl, pyrrolyl, imidazoloyl, pyrazolyl, pyrimidinyl, thiazolyl, quinolinyl, isoquinolinyl, benzofuranyl, benzothienyl, benzodioxanyl, benzodioxoloyl and the like.

In this specification "optionally substituted" means that a group may be further substituted by one or more groups selected from alkyl, alkenyl, alkynyl, aryl, fluoro, chloro, bromo, hydroxy, alkyloxy, alkenyloxy, aryloxy, acyloxy, amino, alkylamino, dialkylamino, arylamino, thio, alkylthio, arylthio, cyano, nitro, acyl, amido, alkylamido, dialkylamido, carboxyl, or two optional substituents may together with the carbon atoms to which they are attached form a 5- or 6-membered aromatic or non-aromatic ring containing 0, 1 or 2 heteroatoms selected from nitrogen, oxygen or sulfur. Optional substituents may themselves bear additional optional substituents. Preferred optional substituents include $C_{1-3}$ alkyl such as for example methyl, ethyl and trifluoromethyl, fluoro, chloro, bromo, hydroxy, $C_{1-3}$ alkyloxy such as for example methoxy, ethoxy and trifluoromethoxy, and amino.

Throughout the specification, the term "alkyl", used either atone or in compound words such as "alkyloxy" is denoted, unless otherwise defined, to mean both the straight chain $C_{1-6}$ alkyl or branched chain $C_{3-6}$ alkyl and the branched or unbranched $C_{3-6}$ cycloalkyl and includes optionally substituted alkyl. Examples of straight chain $C_{1-6}$ alkyl and branched chain $C_{3-6}$ alkyl include methyl, ethyl, propyl, isopropyl, butyl, isobutyl, sec-butyl, tert-butyl, hexyl, 4-methylpentyl, 1-methylpentyl, 2-methylpentyl, 3-methylpentyl and the like. Examples of $C_{3-6}$ cycloalkyl include cyclopropyl, cyclobutyl, cyclopentyl, cyclohexyl and the like Haloalkyl groups such as trifluromethyl are examples of optionally substituted alkyl groups.

Throughout the specification, the term "alkenyl", used either alone or in compound words such as "alkenyloxy" is denoted, unless otherwise defined, to mean both the straight chain $C_{2-6}$alkenyl or branched chain $C_{3-6}$alkenyl and the branched or unbranched $C_{3-6}$cycloalkenyl and includes optionally substituted alkenyl. Examples of straight chain $C_{2-6}$alkenyl and branched chain $C_{3-6}$alkenyl include ethylenyl, propenyl, isopropenyl, butenyl, isobutenyl, dimethylbutenyl, pentenyl, methylpentenyl, hexenyl and the like. Examples of $C_{3-6}$cycloalkyl include cyclobutenyl, cyclopentenyl, cyclohexenyl and the like.

"Oxoalkyl" and "oxoalkenyl" mean an alkyl or alkenyl group which includes a carbonyl group other than as the linking group.

"Acyl" means a group represented by C(=O)alkyl or C(=O)alkenyl. Acyl groups derived from amino acids are included within the meaning of "acyl".

The following groups wherein each R in each group may be the same or different and is independently selected from hydrogen or alkyl are representative examples of the groups which may be utilised as the antioxidant group, E, of the compounds of formula (1). Preferably at least one R group is alkyl. More preferably at least two R groups are alkyl. Preferably the alkyl groups are $C_{1-4}$alkyl. Preferably the alkyl groups are not substituted. The preferred point of attachment of the antioxidant moiety is indicated by an arrow:

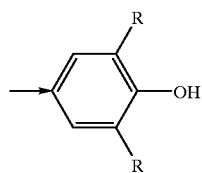
a

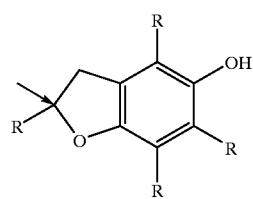
b

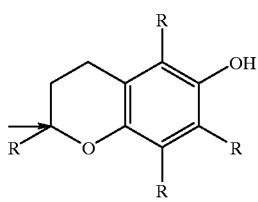
c

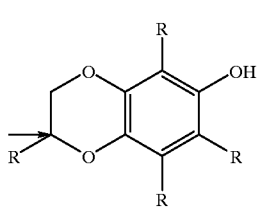
d

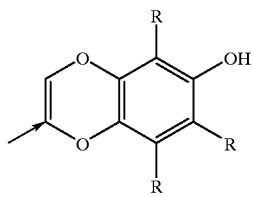
e

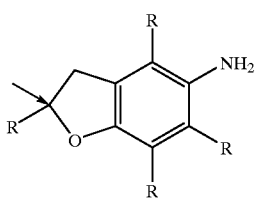
f

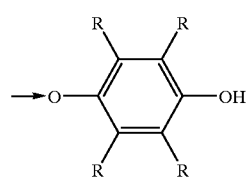
g

The following groups are respresenative examples of the groups B, the preferred point of attachment of the moiety is indicated by an arrow:

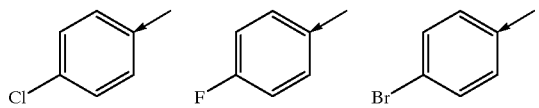

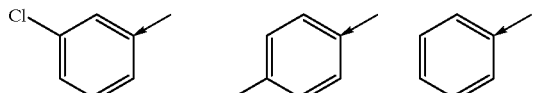

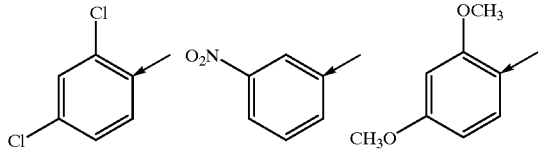

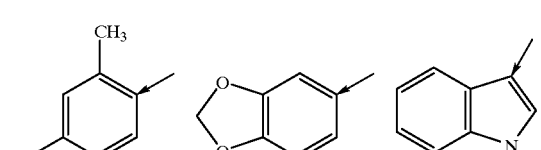

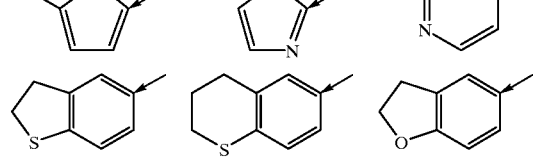

-continued

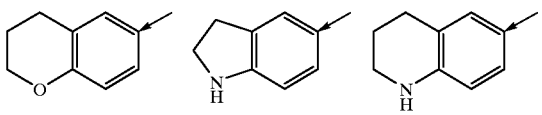

A preferred group of compounds of formula (1) are those wherein:

B is phenyl or optionally substituted phenyl
$R^1$ is hydroxy;
$R^2$ and $R^3$ are the same or different and are independently selected from hydrogen or $C_{1-3}$ alkyl;
m is 0, 1 or 2. Preferably m is 0 or 1;
D is a linking chain of atoms which may be optionally substituted and contains from 1–8 atoms in the chain, and wherein preferably the atoms of the chain are carbon, oxygen, nitrogen or sulfur, more preferably the atoms of the chain are carbon atoms present either as a carbonyl, a straight chain or branched alkyl, oxoalkyl, alkenyl or oxoalkenyl group of 1–6 carbons; examples of D include $(CH_2)_n$, $C(=O)(CH_2)_{n-1}$, $C(=O)CH=CH$ or $(CH_2)_nCH=CH$ wherein n is 1–6;
E is a phenolic antioxidant group or an amino derivative thereof with antioxidant properties.

A further preferred group of compounds of formula (1) are those wherein:

B is unsubstituted phenyl, phenyl optionally substituted in the para position, or 2,3-dihydro-5-benzo[b]thienyl;
$R^1$ is hydroxy;
one of $R^2$ and $R^3$ is selected from hydrogen or $C_{1-3}$ alkyl and the other is hydrogen;
D is $(CH_2)_n$,$C(=O)(CH_2)_{n-1}$,$C(=O)CH=CH$ or $(CH_2)_nCH=CH$ wherein n is 1 or 2;
m is 0 or 1;
E is selected from the group a, b, c, d, e, f or g, preferably a, b, c, f, or g, most preferably b, c, f or g.

The salts of the compounds of formula (1) are preferably pharmaceutically acceptable, but it will be appreciated that non-pharmaceutically acceptable salts also fall within the scope of the present invention, since these are useful as intermediates in the preparation of pharmaceutically acceptable salts. The pharmaceutically acceptable salts may include conventional non-toxic salts or quaternary ammonium salts of these compounds, which may be formed, e.g. from organic or inorganic acids or bases. Examples of such acid addition salts include, but are not limited to, those formed with pharmaceutically acceptable acids such as acetic, propionic, citric, lactic, methanesulphonic, toluenesulphonic, benzenesulphonic, salicylic, ascorbic, hydrochloric, orthophosphoric, sulfuric, tartaric and hydrobromic acids. Base salts includes, but is not limited to, those formed with pharmaceutically acceptable cations, such as sodium, potassium, lithium, calcium, magnesium, ammonium and alkylammonium. Also, basic nitrogen-containing groups may be quaternised with such agents as lower alkyl halides, such as methyl, ethyl, propyl, and butyl chlorides, bromides and iodides; dialkyl sulfates like dimethyl and diethyl sulfate; and others.

The compounds of the invention may be in crystalline form or as solvates (e.g. hydrates) and it is intended that both forms are within the scope of the present invention. Methods of solvation are generally known within the art.

Pharmaceutically acceptable derivatives may include any pharmaceutically acceptable salt, hydrate or any other compound which, upon administration to a subject, is capable of providing (directly or indirectly) a compound of formula (1) or an therapeutically active metabolite or residue thereof.

Any compound that is a prodrug of a compound of formula (1) is within the scope and spirit of the invention. The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester derivative.

The compounds of the present invention may exist as an isomer or mixtures of isomers. All such isomeric forms of the compounds of formula (1) are included as part of the present invention. As the compounds of the invention may have one or more chiral centres they are capable of existing in enantiomeric and diastereomeric forms, all such forms whether purified or as mixtures are included within the scope of the terms "isomer" and "isomers" with regard to the present invention. Isomers may be separated or selectively prepared using procedures routinely used by those skilled in the art.

Examples of compounds of general formula (1) which fall within the ambit of the present invention include those listed in Table 1 below.

TABLE 1

| Compound | B | $R^1$ | $R^2$ | $R^3$ | m | D | E |
|---|---|---|---|---|---|---|---|
| 1 | | OH | H | H | 0 | $CH_2$ | |
| 2 | | OH | H | $CH_3$ | 0 | | |
| 3 | | OH | H | H | 1 | | |
| 4 | | OH | H | $CH_3$ | 1 | | |
| 5 | | OH | H | H | 0 | C=O | 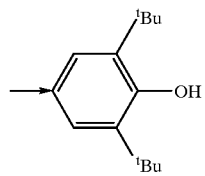 |
| 6 | | OH | H | $CH_3$ | 0 | | |
| 7 | | OH | H | H | 1 | | |
| 8 | | OH | H | $CH_3$ | 1 | | |
| 9 | | OH | H | H | 0 | $CH_2CH=CH$ | |
| 10 | | OH | H | $CH_3$ | 0 | | |
| 11 | | OH | H | H | 1 | | |
| 12 | | OH | H | $CH_3$ | 1 | | |
| 13 | | OH | H | H | 0 | $C(O)CH=CH$ | |
| 14 | | OH | H | $CH_3$ | 0 | | |

TABLE 1-continued

| Compound | B | R¹ | R² | R³ | m | D | E |
|---|---|---|---|---|---|---|---|
| 15 | | OH | H | H | 1 | | |
| 16 | | OH | H | CH₃ | 1 | | |
| 17 | | OH | H | H | 0 | CH₂ | |
| 18 | | OH | H | CH₃ | 0 | | |
| 19 | | OH | H | H | 1 | | |
| 20 | | OH | H | CH₃ | 1 | | |
| 21 | | OH | H | H | 0 | C=O | |
| 22 | | OH | H | CH₃ | 0 | | |
| 23 | | OH | H | H | 1 | | |
| 24 | | OH | H | CH₃ | 1 | | 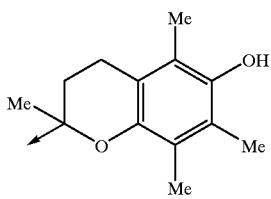 |
| 25 | | OH | H | H | 0 | CH₂CH=CH | |
| 26 | | OH | H | CH₃ | 0 | | |
| 27 | | OH | H | H | 1 | | |
| 28 | | OH | H | CH₃ | 1 | | |
| 29 | | OH | H | H | 0 | C(O)CH=CH | |
| 30 | | OH | H | CH₃ | 0 | | |
| 31 | | OH | H | H | 1 | | |
| 32 | | OH | H | CH₃ | 1 | | |
| 33 | | OH | H | H | 0 | CH₂ | |
| 34 | | OH | H | CH₃ | 0 | | |
| 35 | | OH | H | H | 1 | | |
| 36 | | OH | H | CH₃ | 1 | | |
| 37 | | OH | H | H | 0 | C=O | |
| 38 | | OH | H | CH₃ | 0 | | |
| 39 | | OH | H | H | 1 | | |
| 40 | | OH | H | CH₃ | 1 | | 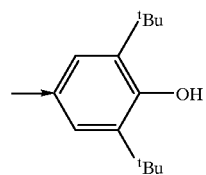 |
| 41 | | OH | H | H | 0 | CH₂CH=CH | |
| 42 | | OH | H | CH₃ | 0 | | |
| 43 | | OH | H | H | 1 | | |
| 44 | | OH | H | CH₃ | 1 | | |
| 45 | | OH | H | H | 0 | C(O)CH=CH | |
| 46 | | OH | H | CH₃ | 0 | | |
| 47 | | OH | H | H | 1 | | |
| 48 | | OH | H | CH₃ | 1 | | |
| 49 | | OH | H | H | 0 | CH₂ | |
| 50 | | OH | H | CH₃ | 0 | | |
| 51 | | OH | H | H | 1 | | |
| 52 | | OH | H | CH₃ | 1 | | |
| 53 | | OH | H | H | 0 | C=O | |
| 54 | | OH | H | CH₃ | 0 | | |
| 55 | | OH | H | H | 1 | | |
| 56 | | OH | H | CH₃ | 1 | | 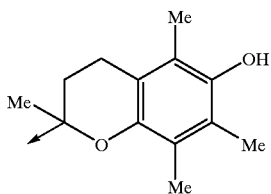 |
| 57 | | OH | H | H | 0 | CH₂CH=CH | |
| 58 | | OH | H | CH₃ | 0 | | |
| 59 | | OH | H | H | 1 | | |
| 60 | | OH | H | CH₃ | 1 | | |
| 61 | | OH | H | H | 0 | C(O)CH=CH | |
| 62 | | OH | H | CH₃ | 0 | | |
| 63 | | OH | H | H | 1 | | |
| 64 | | OH | H | CH₃ | 1 | | |
| 65 | | OH | H | H | 0 | CH₂ | |
| 66 | | OH | H | CH₃ | 0 | | |
| 67 | | OH | H | H | 1 | | |

TABLE 1-continued

| Compound | B | R¹ | R² | R³ | m | D | E |
|---|---|---|---|---|---|---|---|
| 68 | | OH | H | CH₃ | 1 | | |
| 69 | | OH | H | H | 0 | C=O | |
| 70 | | OH | H | CH₃ | 0 | | |
| 71 | | OH | H | H | 1 | | |
| 72 | | OH | H | CH₃ | 1 | | 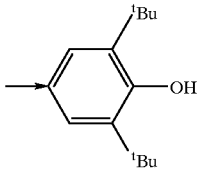 |
| 73 | | OH | H | H | 0 | CH₂CH=CH | |
| 74 | | OH | H | CH₃ | 0 | | |
| 75 | | OH | H | H | 1 | | |
| 76 | | OH | H | CH₃ | 1 | | |
| 77 | | OH | H | H | 0 | C(O)CH=CH | |
| 78 | | OH | H | CH₃ | 0 | | |
| 79 | | OH | H | H | 1 | | |
| 80 | 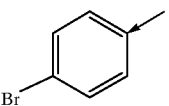 | OH | H | CH₃ | 1 | | |
| 81 | | OH | H | H | 0 | CH₂ | |
| 82 | | OH | H | CH₃ | 0 | | |
| 83 | | OH | H | H | 1 | | |
| 84 | | OH | H | CH₃ | 1 | | |
| 85 | | OH | H | H | 0 | C=O | |
| 86 | | OH | H | CH₃ | 0 | | |
| 87 | | OH | H | H | 1 | | |
| 88 | | OH | H | CH₃ | 1 | | 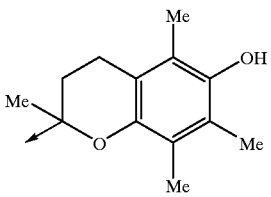 |
| 89 | | OH | H | H | 0 | CH₂CH=CH | |
| 90 | | OH | H | CH₃ | 0 | | |
| 91 | | OH | H | H | 1 | | |
| 92 | | OH | H | CH₃ | 1 | | |
| 93 | | OH | H | H | 0 | C(O)CH=CH | |
| 94 | | OH | H | CH₃ | 0 | | |
| 95 | | OH | H | H | 1 | | |
| 96 | | OH | H | CH₃ | 1 | | |
| 97 | | OH | H | H | 0 | CH₂ | |
| 98 | | OH | H | CH₃ | 0 | | |
| 99 | | OH | H | H | 1 | | |
| 100 | | OH | H | CH₃ | 1 | | |
| 101 | | OH | H | H | 0 | C=O | |
| 102 | | OH | H | CH₃ | 0 | | |
| 103 | | OH | H | H | 1 | | |
| 104 | | OH | H | CH₃ | 1 | | 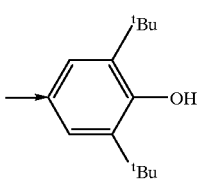 |
| 105 | | OH | H | H | 0 | CH₂CH=CH | |
| 106 | | OH | H | CH₃ | 0 | | |
| 107 | | OH | H | H | 1 | | |
| 108 | | OH | H | CH₃ | 1 | | |
| 109 | | OH | H | H | 0 | C(O)CH=CH | |
| 110 | | OH | H | CH₃ | 0 | | |
| 111 | | OH | H | H | 1 | | |
| 112 | 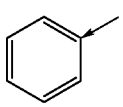 | OH | H | CH₃ | 1 | | |
| 113 | | OH | H | H | 0 | CH₂ | |
| 114 | | OH | H | CH₃ | 0 | | |
| 115 | | OH | H | H | 1 | | |
| 116 | | OH | H | CH₃ | 1 | | |

TABLE 1-continued

| Compound | B | R¹ | R² | R³ | m | D | E |
|---|---|---|---|---|---|---|---|
| 117 | | OH | H | H | 0 | C=O | 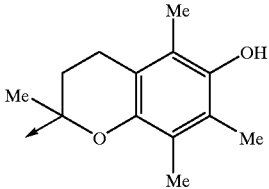 |
| 118 | | OH | H | CH₃ | 0 | | |
| 119 | | OH | H | H | 1 | | |
| 120 | | OH | H | CH₃ | 1 | | |
| 121 | | OH | H | H | 0 | CH₂CH=CH | |
| 122 | | OH | H | CH₃ | 0 | | |
| 123 | | OH | H | H | 1 | | |
| 124 | | OH | H | CH₃ | 1 | | |
| 125 | | OH | H | H | 0 | C(O)CH=CH | |
| 126 | | OH | H | CH₃ | 0 | | |
| 127 | | OH | H | H | 1 | | |
| 128 | | OH | H | CH₃ | 1 | | |
| 129 | | OH | H | H | 0 | CH₂ | |
| 130 | | OH | H | CH₃ | 0 | | |
| 131 | | OH | H | H | 1 | | |
| 132 | | OH | H | CH₃ | 1 | | |
| 133 | | OH | H | H | 0 | C=O | 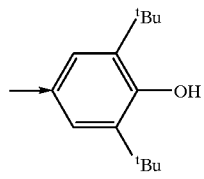 |
| 134 | | OH | H | CH₃ | 0 | | |
| 135 | | OH | H | H | 1 | | |
| 136 | | OH | H | CH₃ | 1 | | |
| 137 | | OH | H | H | 0 | CH₂CH=CH | |
| 138 | | OH | H | CH₃ | 0 | | |
| 139 | | OH | H | H | 1 | | |
| 140 | | OH | H | CH₃ | 1 | | |
| 141 | | OH | H | H | 0 | C(O)CH=CH | |
| 142 | | OH | H | CH₃ | 0 | | |
| 143 | | OH | H | H | 1 | | |
| 144 | 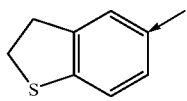 | OH | H | CH₃ | 1 | | |
| 145 | | OH | H | H | 0 | CH₂ | |
| 146 | | OH | H | CH₃ | 0 | | |
| 147 | | OH | H | H | 1 | | |
| 148 | | OH | H | CH₃ | 1 | | |
| 149 | | OH | H | H | 0 | C=O | 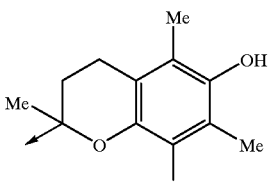 |
| 150 | | OH | H | CH₃ | 0 | | |
| 151 | | OH | H | H | 1 | | |
| 152 | | OH | H | CH₃ | 1 | | |
| 153 | | OH | H | H | 0 | CH₂CH=CH | |
| 154 | | OH | H | CH₃ | 0 | | |
| 155 | | OH | H | H | 1 | | |
| 156 | | OH | H | CH₃ | 1 | | |
| 157 | | OH | H | H | 0 | C(O)CH=CH | |
| 158 | | OH | H | CH₃ | 0 | | |
| 159 | | OH | H | H | 1 | | |
| 160 | | OH | H | CH₃ | 1 | | |
| 161 | | OH | H | H | 0 | CH₂ | |
| 162 | | OH | H | CH₃ | 0 | | |
| 163 | | OH | H | H | 1 | | |
| 164 | | OH | H | CH₃ | 1 | | |
| 165 | | OH | H | H | 0 | C=O | 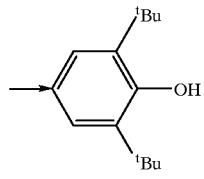 |
| 166 | | OH | H | CH₃ | 0 | | |
| 167 | | OH | H | H | 1 | | |
| 168 | | OH | H | CH₃ | 1 | | |
| 169 | | OH | H | H | 0 | CH₂CH=CH | |

TABLE 1-continued
| Compound | B | R¹ | R² | R³ | m | D | E |
|---|---|---|---|---|---|---|---|
| 170 | | OH | H | CH₃ | 0 | | |
| 171 | | OH | H | H | 1 | | |
| 172 | | OH | H | CH₃ | 1 | | |
| 173 | | OH | H | H | 0 | C(O)CH=CH | |
| 174 | | OH | H | CH₃ | 0 | | |
| 175 | | OH | H | H | 1 | | |
| 176 | 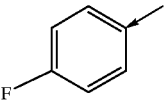 | OH | H | CH₃ | 1 | | |
| 177 | | OH | H | H | 0 | CH₂ | |
| 178 | | OH | H | CH₃ | 0 | | |
| 179 | | OH | H | H | 1 | | |
| 180 | | OH | H | CH₃ | 1 | | |
| 181 | | OH | H | H | 0 | C=O | |
| 182 | | OH | H | CH₃ | 0 | | |
| 183 | | OH | H | H | 1 | | |
| 184 | | OH | H | CH₃ | 1 | | 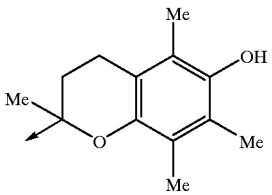 |
| 185 | | OH | H | H | 0 | CH₂CH=CH | |
| 186 | | OH | H | CH₃ | 0 | | |
| 187 | | OH | H | H | 1 | | |
| 188 | | OH | H | CH₃ | 1 | | |
| 189 | | OH | H | H | 0 | C(O)CH=CH | |
| 190 | | OH | H | CH₃ | 0 | | |
| 191 | | OH | H | H | 1 | | |
| 192 | | OH | H | CH₃ | 1 | | |
| 193 | | OH | H | H | 0 | CH₂ | |
| 194 | | OH | H | CH₃ | 0 | | |
| 195 | | OH | H | CH₃ | 1 | | 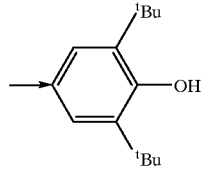 |
| 196 | | OH | H | H | 0 | | |
| 197 | | OH | H | CH₃ | 0 | | |
| 198 | 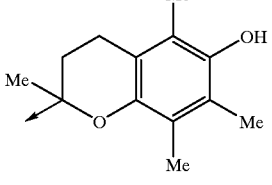 | OH | H | CH₃ | 1 | | 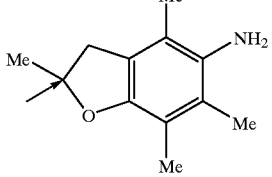 |
| 199 | | OH | H | H | 0 | | |
| 200 | | OH | H | CH₃ | 0 | | |
| 201 | | OH | H | CH₃ | 1 | | 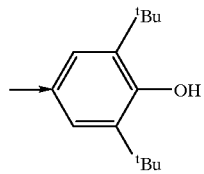 |
| 202 | | OH | H | H | 0 | CH₂ | |
| 203 | | OH | H | CH₃ | 0 | | |
| 204 | | OH | H | CH₃ | 1 | | |

TABLE 1-continued
| Compound | B | R¹ | R² | R³ | m | D | E |
|---|---|---|---|---|---|---|---|
| 205 | 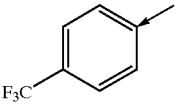 | OH | H | H | 0 | | 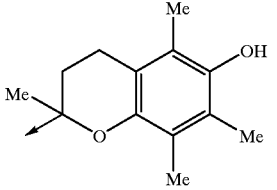 |
| 206 | | OH | H | CH₃ | 0 | | |
| 207 | | OH | H | CH₃ | 1 | | |
| 208 | | OH | H | H | 0 | | 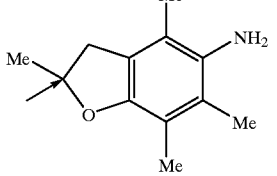 |
| 209 | | OH | H | CH₃ | 0 | | |
| 210 | | OH | H | CH₃ | 1 | | |
| 211 | | OH | H | H | 0 | CH₂ | 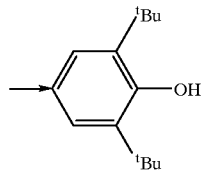 |
| 212 | | OH | H | CH₃ | 0 | | |
| 213 | | OH | H | CH₃ | 1 | | |
| 214 | 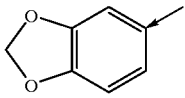 | OH | H | H | 0 | | 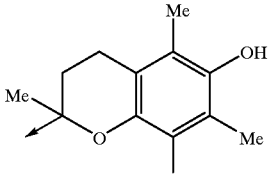 |
| 215 | | OH | H | CH₃ | 0 | | |
| 216 | | OH | H | CH₃ | 1 | | |
| 217 | | OH | H | H | 0 | | 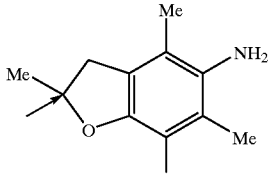 |
| 218 | | OH | H | CH₃ | 0 | | |
| 219 | | OH | H | CH₃ | 1 | | |
| 220 | | OH | H | H | 0 | CH₂ | 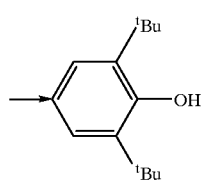 |
| 221 | | OH | H | CH₃ | 0 | | |
| 222 | | OH | H | CH₃ | 1 | | |
| 223 | 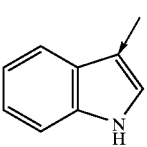 | OH | H | H | 0 | | 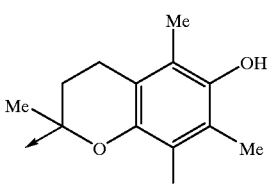 |
| 224 | | OH | H | CH₃ | 0 | | |
| 225 | | OH | H | CH₃ | 1 | | |
| 226 | | OH | H | H | 0 | | 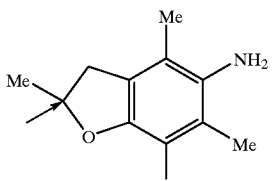 |
| 227 | | OH | H | CH₃ | 0 | | |
| 228 | | OH | H | CH₃ | 1 | | |

TABLE 1-continued
| Compound | B | R¹ | R² | R³ | m | D | E |
|---|---|---|---|---|---|---|---|
| 229 | | OH | H | H | 0 | CH₂ | 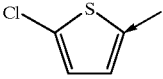 |
| 230 | | OH | H | CH₃ | 0 | | |
| 231 | | OH | H | CH₃ | 1 | | |
| 232 | 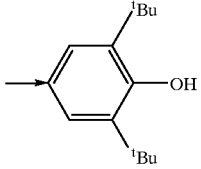 | OH | H | H | 0 | | 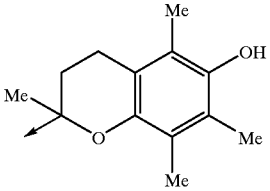 |
| 233 | | OH | H | CH₃ | 0 | | |
| 234 | | OH | H | CH₃ | 1 | | |
| 235 | | OH | H | H | 0 | | 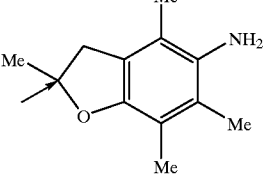 |
| 236 | | OH | H | CH₃ | 0 | | |
| 237 | | OH | H | CH₃ | 1 | | |
| 238 | | OH | H | H | 0 | CH₂ | 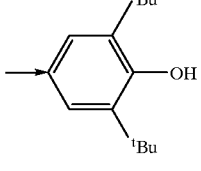 |
| 239 | | OH | H | CH₃ | 0 | | |
| 240 | | OH | H | CH₃ | 1 | | |
| 241 | 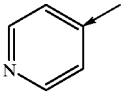 | OH | H | H | 0 | | 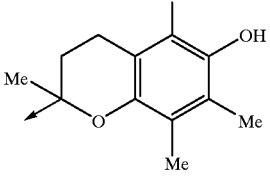 |
| 242 | | OH | H | CH₃ | 0 | | |
| 243 | | OH | H | CH₃ | 1 | | |
| 244 | | OH | H | H | 0 | | 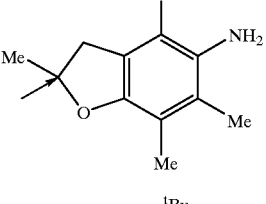 |
| 245 | | OH | H | CH₃ | 0 | | |
| 246 | | OH | H | CH₃ | 1 | | |
| 247 | | OH | H | H | 0 | CH₂ | 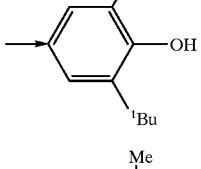 |
| 248 | | OH | H | CH₃ | 0 | | |
| 249 | | OH | H | CH₃ | 1 | | |
| 250 | 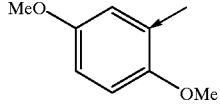 | OH | H | H | 0 | | 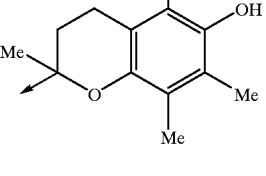 |
| 251 | | OH | H | CH₃ | 0 | | |
| 252 | | OH | H | CH₃ | 1 | | |

TABLE 1-continued

| Compound | B | R¹ | R² | R³ | m | D | E |
|---|---|---|---|---|---|---|---|
| 253 | | OH | H | H | 0 | | (2,2,4,6,7-pentamethyl-2,3-dihydrobenzofuran-5-amine group) |
| 254 | | OH | H | CH₃ | 0 | | |
| 255 | | OH | H | CH₃ | 1 | | |
| 256 | | OH | H | H | 0 | CH₂ | (3,5-di-tert-butyl-4-hydroxyphenyl) |
| 257 | | OH | H | CH₃ | 0 | | |
| 258 | | OH | H | CH₃ | 1 | | |
| 259 | 4-CN-phenyl | OH | H | H | 0 | | (2,2,5,7,8-pentamethylchroman-6-ol) |
| 260 | 4-CN-phenyl | OH | H | CH₃ | 0 | | |
| 261 | 4-CN-phenyl | OH | H | CH₃ | 1 | | |
| 262 | | OH | H | H | 0 | | (2,2,4,6,7-pentamethyl-2,3-dihydrobenzofuran-5-amine) |
| 263 | | OH | H | CH₃ | 0 | | |
| 264 | | OH | H | CH₃ | 1 | | |
| 265 | 4-Cl-phenyl | OH | H | H | 0 | CH₂ | (3-tert-butyl-5-methyl-4-hydroxyphenyl) |
| 266 | 4-Cl-phenyl | OH | H | CH₃ | 0 | | |
| 267 | 4-Cl-phenyl | OH | H | CH₃ | 1 | | |
| 268 | | OH | H | H | 0 | | (2,2,4,6,7-pentamethyl-2,3-dihydrobenzofuran-5-amine) |
| 269 | | OH | H | CH₃ | 0 | | |
| 270 | | OH | H | CH₃ | 1 | | |
| 271 | 4-HO-phenyl | OH | H | H | 0 | CH₂ | (3,5-dimethyl-4-hydroxyphenyl) |
| 272 | 4-HO-phenyl | OH | H | CH₃ | 0 | | |
| 273 | 4-HO-phenyl | OH | H | CH₃ | 1 | | |

Ifenprodil and eliprodil have been reported as antiischaemic agents (Gotti et al., 1988) and both compounds have been reported to associate with the polyamine sensitive site of the NMDA receptor complex (Carter et al., 1989 and 1990; Reynolds et al., 1989; and Robinson et al., 1990). Further reports indicate that compounds that competitively inhibit ifenprodil binding to cortical membranes may also act as antagonists of the polyamine sensitive binding site of the NMDA receptor complex and are potential neuroprotective agents (Beart et al., 1992 and 1995 and WO92/03131). These agents bind independently of the NMDA ion channel (Carter et al., 1991; Reynolds et al., 1989), appear not to cause behavioural effects (Carter et al., 1991), and may target specific heteromeric NMDA receptors (Williams, 1993; Nicola et al., 1994) uniquely distributed in forebrain regions (Standaert et al., 1994) affected in ischaemia and head trauma. The compounds of the present invention inhibit polyamine-sensitive binding of [$^{125}$I]ifenprodil in rat cerebral cortical membranes according to the procedure of Beart et al., 1992 and Mercer et al., 1993. Accordingly, the compounds of the present invention are capable of binding to the NMDA receptor complex and providing a neuroprotective effect.

The compounds of the invention inhibited NMDA induced cell death in cultures of neuronal cells.

Compounds that modulate voltage-sensitive sodium channels may be useful in a number of therapeutic indications including disorders related to neurological damage of the central nervous system. Affinity for voltage-sensitive sodium channels may be determined by measuring the displacement of labelled ligands from their binding sites on the sodium channel, for example the procedure of Catterall et al. (1981) uses [$^3$H]-batrachotoxinin A 20-α-benzoate. Compounds of the present invention show an affinity for voltage-sensitive sodium channels in this type of assay.

Moreover the compounds of the present invention inhibit lipid peroxidation. Compounds that inhibit lipid peroxidation have been shown to afford a beneficial effect on neurological recovery in several in vivo models of cerebral ischaemia as well as providing benefits in other models or in clinical trials relating to neuronal damage (Jacobsen et al., 1992). Lipid peroxidation has been assessed in the present study using two procedures adopted from that described by Ohkawa et al. (1979) and Cheng et al. (1994). The compounds of the present invention have shown significant antioxidant effect in both assay systems.

Accordingly the compounds of the present invention, in view of their NMDA directed, sodium channel and antioxidant activity, are suitable for the control or prevention of disorders related to neurological damage of the central nervous system since they may reduce neuronal damage by excitotoxic mechanisms and reactive free radicals. Those skilled in the art will appreciate that the compounds of the present invention may also be useful in situations where there is a risk of neurological damage of the central nervous system.

The in vivo effects of compounds against cerebral ischaemia may be tested in assays such as the Middle Cerebral Artery Occlusion test (Brown et al., 1995). A compound of the present invention has shown a neuroprotective effect in such an assay.

Systematic administration of NMDA antagonists such as ifenprodil have been shown to protect mice from the methamphetamine-induced loss of neostriatal tyrosine hydroxylase activity in a methamphetamine model of excitotoxic neuronal damage in mice (Sonsalla et al., 1991). A compound of the present invention showed a protective effect in an assay of this kind.

In view of their voltage-sensitive sodium channel activity the compounds of the present invention may also be useful in the control or prevention of other conditions related to sodium channels.

Accordingly, in a further aspect of the present invention there is provided a method for the prophylactic or therapeutic treatment of one or more disorders related to neurological damage of the central nervous system or other conditions related to sodium channels which method includes administering to a subject in need thereof an effective amount of a compound of formula (1) in accordance with the invention.

The present invention also provides the use of a compound of formula (1) in the manufacture of a medicament for use in the treatment of disorders related to neurological damage of the central nervous system or other conditions related to sodium channels.

The present invention further provides a compound of formula (1) for use in the treatment of disorders related to neurological damage of the central nervous system or other conditions related to sodium channels.

The term "disorders related to neurological damage of the central nervous system" is used herein in its broadest sense and includes any disorder or condition that may result from or cause damage to the neurones of the central nervous system.

Examples of disorders that may be treated in accordance with the present invention include, but are not limited to, acute events that lead to ischaemia or other forms of hypoxia such as head trauma, stroke, cardiac arrest, ischaemia, hypoxia, hypoglycaemia, epilepsy and the like, or neurodegenerative diseases such as Alzheimer's disease, Parkinson's disease or Huntington's disease, lateral amyotrophic sclerosis and variants thereof, and schizophrenia. Excitotoxic/free radical-mediated cell death can involve necrosis and apoptosis, and those skilled in the art will appreciate the present molecules may be suitable in conditions where both types of cytotoxic mechanisms occur including the forementioned neurological conditions, normal development and the aging process.

The term "other conditions related to sodium channels" is used herein in its broadest sense and includes any condition or disorder that may benefit from administration of a voltage-sensitive sodium channel modulator.

Examples of other conditions related to sodium channels that may be treated in accordance with the present invention include, but are not limited to, epilepsy or epileptic psychotic symptoms and hypertension. The relief of pain or anti-nociception may also be achieved using sodium channel blockers and are considered also as examples of other conditions related to sodium channels.

Compounds of the invention showed analgesic activity in a formalin pain test in rats (Abbott et al., 1995)

Inhibition of calcium channels including those modulated by the NMDA receptor may be useful in diseases and conditions other than those noted above. Those skilled in the art will appreciate that the compounds of the present invention may be useful in the treatment of such other diseases or conditions where antagonism of calcium channels, particularly those modulated through the NMDA receptor may be of benefit.

Oxidative processes or damage by free radicals generated by oxidative processes have been implicated in numerous other diseases or conditions, for example atherosclerosis has been linked to the oxidative modification of LDL (Low Density Lipoproteins). In view of their antioxidant activity the compounds of the present invention may be useful in diseases or conditions linked to oxidative processes or damage by free radicals.

The subject may be a human or an animal such as a domestic or wild animal, particularly an animal of economic importance.

By an "effective amount" is meant a quantity of active compound which will upon single or multiple dose administration to the subject be effective in the control or prevention of a disorder or condition or in achieving a blood or tissue level in the subject that corresponds to a concentration of the active compound that has been shown to provide control or prevention of a disorder or condition in an assay used to predict activity of chemical compounds against a disorder or condition.

As used herein the term "control or prevention" in relation to a disorder or condition refers to slowing, interrupting, arresting or stopping the progression of the a disorder or condition or to reducing the extent of the a disorder or condition below that of an untreated control and does not necessarily indicate a total elimination or cessation of the disorder or condition.

When a compound of the invention is administered to a human subject the daily dosage can normally be determined by the attending physician with the dosage generally varying according to the age, weight, and response of the individual subject, as well as the severity of the subject's symptoms. In general a suitable dose of the compound of the invention will be in the range of 0.1 to 50 mg per kilogram body weight of the recipient per day, preferably in the range of 0.5 to 10 mg per kilogram body weight per day. In some instances, a sufficient therapeutic effect can be obtained at lower doses while in others, larger doses will be required. The desired dose is preferably presented as two, three, four, five, six or more sub-doses administered at appropriate intervals throughout the day. These sub-doses may be administered in unit dosage forms, for example, containing 1 to 500 mg, preferably about 10 to 1000 mg of active ingredient per unit dosage form.

The compounds according to the invention hereinafter for ease of reference referred to as the "active ingredient", may be administered for therapy by any suitable route, including oral, rectal, nasal, topical (including buccal and sublingual); vaginal and parenteral (including subcutaneous, intramuscular, intravenous and intradermal). It will be appreciated that the preferred route will vary with the condition, the age of the subject and the chosen active ingredient. The treatment method of the invention may be used in combination therapy wherein the compounds of the invention are administered in conjunction with one or more other pharmaceutically active agents.

The present invention also extends to a pharmaceutical or veterinary composition which includes the active ingredient in association with a pharmaceutically or veterinarily acceptable carrier, diluent, adjuvant and/or excipient.

The compositions of the present invention may include at least one compound of general formula (1); together with one or more pharmaceutically acceptable carriers, diluents, adjuvants and/or excipients therefor, and optionally other therapeutic agents. Each carrier, diluent, adjuvant and/or excipient must be pharmaceutically "acceptable" in the sense of being compatible with the other ingredients of the composition and not injurious to the subject. Compositions include those suitable for oral, rectal, nasal, topical (including buccal and sublingual); vaginal or parenteral (including subcutaneous, intramuscular, intravenous and intradermal) administration. The compositions may conveniently be presented in unit dosage form and may be prepared by methods well known in the art of pharmacy. Such methods include the step of bringing into association the active ingredient with the carrier, diluent, adjuvant and/or excipient which includes one or more accessory ingredients. In general, the compositions are prepared by uniformly and intimately bringing into association the active ingredient with liquid carriers, diluents, adjuvants and/or excipients or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

Tablets may be made by compression or moulding, optionally with one or more accessory ingredients. Compressed tablets may be prepared by compressing in a suitable machine the active ingredient in a free-flowing form such as a powder or granules, optionally mixed with a binder (e.g inert diluent, preservative disintegrant (e.g. sodium starch glycollate, cross-linked povidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured basis, usually sucrose and acacia or tragacanth gum; pastilles comprising the active ingredient in an inert basis such as gelatine and glycerin, or sucrose and acacia gum; and mouthwashes comprising the active ingredient in a suitable liquid carrier.

Compositions for rectal administration may be presented as a suppository with a suitable base comprising, for example, cocoa butter.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous sterile injection solutions which preferably are isotonic and which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as hereinabove described, or an appropriate fraction thereof, of an active ingredient.

The compounds according to the invention may also be presented for use in the form of veterinary compositions, which may be prepared, for example, by methods that are conventional in the art. Examples of such veterinary compositions include those adapted for:

(a) oral administration, external application, for example drenches (e.g., aqueous or non-aqueous solutions or suspensions); tablets or boluses; powders, granules or pellets for admixture with feed stuffs; pastes for application to the tongue;

(b) parenteral administration for example by subcutaneous, intramuscular or intravenous injection, e.g. as a sterile solution or suspension; or (when appropriate) by intra-mammary injection where a suspension or solution is introduced into the udder via the teat;

(c) topical application, e.g. as a cream, ointment or spray applied to the skin; or (d) intravaginally, e.g. as a pessary, cream or foam.

It should be understood that in addition to the ingredients particularly mentioned above, the compositions of this invention may include other agents conventional in the art having regard to the type of composition in question, for example, those suitable for oral administration may include such further agents as binders, sweeteners, thickeners, flavouring agents, disintegrating agents, coating agents, preservatives, lubricants and/or time delay agents.

Suitable sweeteners include sucrose, lactose, glucose, aspartame or saccharin. Suitable disintegrating agents include corn starch, methylcellulose, polyvinylpyrrolidine, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or glutan. Suitable preservatives include sodium benzoate, vitamin E, alpha-tocopherol, ascorbic acid, methyl paraben, propyl paraben or sodium bisulphite. Suitable lubricants include magnesium stearate, steric acid, sodium oleate, sodium chloride or talc. Suitable time delay agents include glyceryl monostearate or glyceryl distearate.

In another aspect of the present invention there is provided a method for the manufacture of the compounds of formula (1). The method of the invention may be in accordance with scheme 1 or scheme 2 as set out below.

Scheme 1

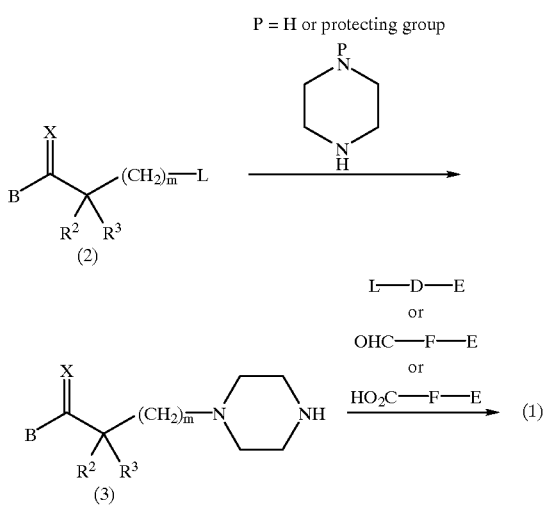

Piperazine, optionally protected on one of the amino groups, may be reacted with an activated arylalkyl derivative (2); where L is a leaving group such as Cl, Br, I or organic sulfonate (such as mesylate or tosylate); X is $R^1$ (as defined above) and H or is a carbonyl group, $R^2$, $R^3$ and m are as defined above, to provide amine (3). Where appropriate the carbonyl group X may be reduced using a reducing agent such as sodium borohydride, or lithium aluminium hydride or enantioselective reducing agents such as chiral boranes prior to the further reaction of amine (3).

The antioxidant (Group E) and the group D may then be attached to the amine (3); where necessary following removal of protecting groups, according to one of the methods described below. The methods may follow the general methodology described in WO 95/15958.

Method 1

Amines of formula (3) may be reacted with the activated derivative L—D—E, where L, D and E are as defined above, under standard conditions using solvents such as acetonitrile, dimethylformamide, ether or tetrahydrofuran in the presence of a base such as potassium carbonate, sodium carbonate or a tertiary amine, for example triethylamine. The use of certain protecting groups and deprotection steps may be necessary, as will be appreciated by those skilled in the art.

Method 2

Amines of formula (3) may be reacted with the aldehyde OHC—F—E, wherein E is as defined above, and F is $(CH_2)_{n-1}$ or $(CH_2)_{n-1}CH=CH$, and then the resulting species can be reduced using a reducing agent such as sodium acetoxy borohydride, sodium cyanoborohydride, or Red-Al to give the product, (1). The use of certain protecting groups and deprotection steps may be necessary, as will be appreciated by those skilled in the art.

Method 3

Amines of formula (3) may be reacted with the acid $HO_2C$—F—E, wherein E and F are as defined above, using standard conditions such as 1,3-dicyclohexylcarbodiimide or 1-(3-dimethylaminopropyl)-3-ethylcarbodiimide and 1-hydroxybenzotriazole or 4-dimethylaminopyridine in a solvent such as dimethylformamide, acetonitrile, methylene chloride or a mixture thereof. The resulting amide may, where appropriate, be reduced using a reducing agent such as lithium aluminium hydride, borane-dimethylsulfide or Red-Al. The use of certain protecting groups and deprotection steps may be necessary, as will be appreciated by those skilled in the art.

Alternatively, optionally protected piperazine may be reacted with the activated derivative L—D—E, the aldehyde OHC—F—E, or the acid $HO_2C$—F—E. The resulting amine may then, following any necessary deprotection or reduction steps using the general methods outlined above, be reacted with the activated arylalkyl derivative (2) (Scheme 2); reduction of the group X, if required, may be performed using the general methods outlined above.

Scheme 2

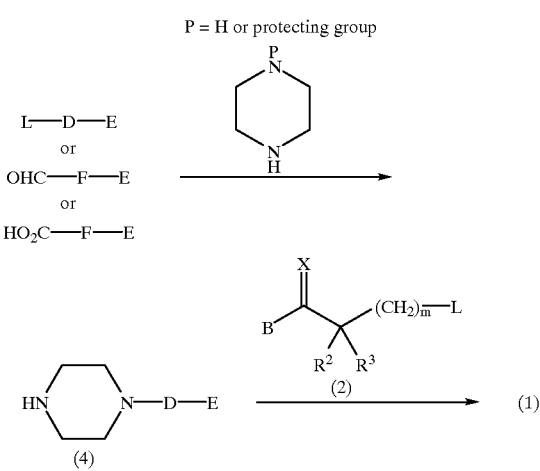

The activated arylalkyl derivatives of formula (2) may be commercially available, for example 2,4'-dichloroacetophenone (Aldrich Chemical Company Inc. of Milwaukee, Wis., USA., hereinafter referred to as Aldrich) or may be prepared by methods known in the art or by simple modifications of such methods. For example, arylalkylketones such as substituted or unsubstituted acetophenones, propiophenones or butyrophenones may be halogenated α to the carbonyl group to provide compounds of formula (2) where m=0 and L is halogen. Activated heteroarylalkyl derivatives of formula (2); for example 5-(α-bromopropionyl)-2,3-dihydro-5-benzo[b]thiophene, may be prepared according to the methods described in U.S. Pat. No. 4,638,070.

The activated derivative L—D—E, the aldehyde OHC—F—E, or the acid $HO_2C$—F—E may be commercially available, for example 3,5-di-tert-butyl4-hydroxybenzaldehyde (Aldrich) and trolox (Aldrich); produced by methods known in the art, such as those described by Jacobsen et al., (1992); in WO 95/15958 and AU 61905/94, or by simple modification of such methods. For example, 3,5-di-tert-butyl4-hydroxybenzaldehyde may be reduced, using for example sodium borohydride, and the resulting benzyl alcohol converted to a group L using standard procedures, for example treatment with phosphorus tribromide provides the compound where L is a bromo group.

The products of the reactions hereinbefore described may be isolated by any of the standard procedures known in the art. Such procedures include extraction, recrystallisation and any type of chromatographic separation routinely utilised in organic synthesis, for example column chromatography, flash column chromatography, reverse phase HPLC.

Protecting groups suitable for the protection of a particular group during a particular reaction may be such as those suggested by Greene, 1991. A protecting group may be removed using conditions known in the art to be suitable for the removal of that particular group. An example of the protecting group P suitable for use with the piperazine is ethyl carboxylate, which may be removed by acid or base catalysed hydrolysis.

Novel compounds of formula (3) and formula (4) are also considered to form part of the present invention.

Throughout this specification, unless the context requires otherwise, where the groups D and F appear in Schemes or formulas they should be read assuming the groups D or F are to be inserted as they are written. In other words from left to right making the appropriate bonds to each end of D or F.

EXAMPLES

Examples are provided to assist in the further understanding of the invention. Particular materials, and conditions employed are intended to be illustrative of the invention and not limitative of the reasonable scope thereof.

Example 1

1-(2-(4-Chlorophenyl)-2-hydroxy-1-methyl)ethyl-4-(3,5-bis(1,1-dimethylethyl)-4-hydroxyphenyl)methylpiperazine (Compound 34)

Step A: 4'-Chloro-2(piperazin-1-yl)propiophenone

A solution of 2-bromo-4'-chloropropiophenone, (741 mg, 3 mmol); ethyl 1-piperazinecarboxylate (474 mg, 3 mmol); triethylamine (0.42 mL, 3 mmol) in diethyl ether (10 mL) was heated at reflux for 3 hours (reaction was monitored by Thin Layer Chromatography (TLC)). The reaction mixture was cooled and further diluted with ethyl acetate and washed with water, brine and dried over $Na_2SO_4$. After evaporation of the solvent in vacuo, the crude viscous liquid was treated with conc. HCl (15 mL) at refluxing temperature for 48 hrs. The cooled reaction mixture was made alkaline by addition of 50% NaOH and extracted with ethyl acetate. The combined extracts were washed with water, brine and dried over $Na_2SO_4$. After evaporation of the solvent 4'chloro-2-(piperazin-1-yl)propiophenone was obtained as a semisolid which was reacted without further purification.

NMR (CDCl$_3$, 200 MHz) δ8.05 (d, J=8.6 Hz, 2H); 7.39 (d, J=8.6 Hz, 2H); 3.97 (q, J=6.7 Hz, 1H); 2.83 (br m, 4H); 2.53 (br m, 4H); 2.07 (br. peak, 1H); 1.23 (d, J=6.7 Hz, 3H).

Step B 4-(bromomethyl)-2,6-bis(1,1-dimethylethyl)phenol was simply prepared from commercially available 3,5-di-tert-butyl-4-hydroxybenzaldehyde (Aldrich) by sodium borohydride reduction followed treatment of the resulting benzyl alcohol with phosphorus tribromide.

Step C

A solution of 4'-chloro-2-(piperazin-1-yl)propiophenone (456 mg, 2 mmol) and 4-(bromomethyl)-2,6-bis(1,1-dimethylethyl)phenol (550 mg, 2 mmol) in THF (10 mL) was stirred at ambient temperature for 4 hrs (reaction monitored by TLC). The reaction mixture was concentrated, neutralised with aqueous bicarbonate and extracted with ethyl acetate. The combined extracts were washed with water, brine and dried over $Na_2SO_4$. After evaporation of the solvent the crude mixture was subjected to LiAlH$_4$ (1.25 mmol) reduction using diethyl ether (10 mL) as solvent at 0° C. under N$_2$ atmosphere (2 hrs). The reaction was quenched by dropwise addition of ice-cold water (2 mL) and $Na_2SO_4$. The mixture was further diluted with ethyl acetate (50 mL) and filtered. The filtrate was separated, washed with water, brine and dried over $Na_2SO_4$. After evaporation of the solvent in vacuo, the crude product was subjected to flash chromatography on silica gel, elution with 70% ethyl acetate/petroleum ether to obtain 1-(2-(4-chlorophenyl)-2-hydroxy-1-methyl)ethyl-4-(3,5-bis(1,1-dimethylethyl)-4-hydroxyphenyl)methylpiperazine as a white solid (585 mg, 90%).

M.p. 66–67° C. NMR(CDCl$_3$, 200 MHz) δ7.29 (s, 4H); 7.10 (s, 2H); 5.17 (s, 1H); 4.20 (d, J=9.7 Hz, 1H); 3.51 (s, 2H); 2.79–2.04 (m, 9H); 1.45 (s, 18H); 0.78 (d, J=6.6 Hz, 3H).

Salt Formation

Salt forms of the compounds of the invention may be formed from the free base form of the compounds of the invention by techniques conventionally used in the art. In some instances it may be convenient to isolate the compounds of the invention directly as a salt rather than as the free base. Examples of salt formation are:

Tartaric acid salts (general procedure).

Tartrate salts were prepared by adding a solution of tartaric acid (2 eq) in a suitable solvent, for example ethanol, to a solution of free base (1 eq) in a suitable solvent, for example ethyl acetate. The homogenous solution was stirred at 60° C. for 15 min. The tartrate salt precipitated out of the solvent which was filtered and dried in vacuo.

Hydrochloride acid salts (general procedure).

Hydrochloride salts were prepared by adding hydrochloric acid, for example anhydrous hydrochloric acid in diethyl ether, to a solution of free base in a suitable solvent, for example ethyl acetate. The solution was stirred for 15 minutes and then concentrated. The hydrochloride salt precipitated out of the solvent, was filtered and dried in vacuo.

Example 2

1-(2-(4-hydroxyphenyl)-2-hydroxy)ethyl-4-(3,5-bis(1,1-dimethylethyl)-4-hydroxyphenyl)methylpiperazine (Compound 1)

The title compound was prepared from 4'-hydroxyphenacyl bromide (prepared by the method of Perti et al, 1967) according to the general methodology of example 3.

M.p. 194–195° C. NMR (CDCl$_3$, 300 MHz) δ7.12 (d, J=8.5 Hz, 2H); 7.09 (s, 2H); 6.64 (d, J=8.5 Hz, 2H); 5.16 (s, 1H); 4.61 (dd, J=9.2, 4.4 Hz, 1H); 3.53 (d, J=13.4 Hz, 1H); 3.48 (d, J=13.4 Hz, 1H); 2.81–2.42 (m, 10H); 1.39 (s, 18H). MS (EI) m/e 440, 422, 303, 219 (100%).

Example 3

1-(2-(4-Chlorophenyl)-2-hydroxy)ethyl-4-(3,5-bis(1,1-dimethylethyl)-4-hydroxyphenyl)methylpiperazine (Compound 33)

4'-Chloro-2-(piperazin-1-yl)acetophenone was prepared as for 4'-chloro-2-(piperazin-1-yl)propiophenone except that commercially available 2-bromo-4'-chloroacetophenone (Aldrich, 10,127-3) is used instead of 2-bromo-4'-chloropropiophenone.

NMR (CDCl$_3$, 200 MHz) δ7.88 (d, J=8.6 Hz, 2H); 7.35 (d, J=8.6 Hz, 2H); 3.69 (s, 2H); 2.93 (m, 4H); 2.54 (m, 4H).

The title compound was prepared by the general methodology of example 3 except that 4'-chloro-2-(piperazin-1-yl)acetophenone was used.

M.p. 149–150° C. NMR (CDCl$_3$, 300 MHz) δ7.3 (s, 4H); 7.10(s, 2H); 5.17 (s, 1H); 4.71 (dd, J=10.3, 3.4 Hz, 1H); 3.51 (s, 2H); 2.83–2.43 (m, 10H); 1.4 (s, 18H). MS (EI) m/e 458, 440, 317, 219 (100%).

Ditartrate salt: M.p. 170–172° C.

Example 4

1-(3-(4-Chlorophenyl)-3-hydroxy)propyl-4-(3,5-bis(1,1-dimethylethyl)-4-hydroxyphenyl)methylpiperazine (Compound 35)

4'-Chloro-3-(piperazin-1-yl)propiophenone was prepared from commercially available 3,4'-dichloropropiophenone (Aldrich, 14,159-3) and piperazine according to the general methodology described at step A of example 1.

The title compound was prepared by the general methodology of example 1 except that 4'-chloro-3-(piperazin-1-yl)propiophenone was used.

M.p. 120° C. NMR (CDCl$_3$, 300 MHz) δ7.3 (s, 4H); 7.1 (s, 2H); 5.15 (s, 1H); 4.91 (dd, J=7, 4.3 Hz, 1H); 3.46, (s, 2H); 2.73–2.2 (m, 10H); 1.84–1.81 (m, 2H); 1.45 (s, 18H). MS (EI) m/e 472, 331, 260, 247, 219 (100%).

Dihydrochloride salt: M.p. 196–197° C.

Example 5

1-(2-(4-bromophenyl)-2-hydroxy)ethyl-4-(3,5-bis(1,1-dimethylethyl)-4-hydroxyphenyl)methylpiperazine (Compound 65)

The title compound was prepared by the general methodology of example 3 starting from commercially available 2-bromo-4'-bromoacetophenone (Aldrich) rather than 2-bromo-4'-chloropropiophenone.

M.p. 148–150° C. NMR (CDCl$_3$, 300 MHz) δ7.45 (d, J=8.4 Hz, 2H); 7.24 (d, J=8.4 Hz, 2H); 7.08 (s, 2H); 5.14 (s, 1H); 4.67 (dd, J=10.4, 3.4 Hz, 1H); 3.46 (s, 2H); 2.9–2.65 (m, 2H); 2.6–2.36 (m, 8H); 1.44 (s, 18H). MS (EI) m/e 503, 485, 317, 219 (100%).

Ditartrate salt: M.p. 179–181° C.

Examples 6–16

The following general methodology was used to prepare the free base

Step A: 1-(3,5-bis(1,1-dimethylethyl)-4-hydroxyphenyl)methylpiperazine

Commercially available (1,1-dimethylethoxy)carbonylpiperazine (12.47 g) and 3,5-bis(1,1-dimethylethyl)-4-hydroxybenzaldehyde (15.67 g) were dissolved in 1:1 mixture of methanol and THF (200 ml). The solution was cooled in an ice-bath, and sodium cyanoborohydride (6.2 g) was added portionwise over 2 h. The reaction mixture was allowed to warm to room temperature and stirred for 48 h. At this time 50 ml of a saturated solution of NaHCO$_3$ was added, and the mixture was concentrated in vacuo. The residue was diluted with water and extracted with dichloromethane. The organic fractions (3×500 ml) were washed with water, brine and dried over sodium sulphate. After removal of the solvent in vacuo, the viscous material was dissolved in trifluoroacetic acid (100 ml) and stirred at room temperature overnight. The reaction mixture was concentrated in vacuo and the residue was triturated with diethyl ether to afford a white solid. A small amount of this trifluoroacetic acid salt was converted into the corresponding free base and analysed as the required product. The product can be isolated as its free base by simple modification of the above described procedure.

NMR (CDCl$_3$, 300 MHz) δ7.07 (s, 2H); 5.2 (br s, 1H); 3.42 (s, 2H); 2.91-2.86 (m, 4H); 2.43 (br s, 4H); 2.2 (br, 1H); 1.43 (s, 18H).

Step B: General Method for the Preparation of Final Target Compounds

A solution of the α-halo derivative of the corresponding arylalkyl ketone (1 eq); the 1-(3,5-bis(1,1-dimethylethyl)-4-hydroxyphenyl)methylpiperazine (1 eq) (either as its free base or trifluoroacetic acid salt) and triethylamine (1–3 eq) in a suitable solvent, for example THF, was stirred at room temperature until the disappearance of starting materials (reaction monitored by TLC). The reaction mixture was filtered and the filtrate concentrated in vacuo. The crude material was redissolved in a suitable solvent, for example ethyl acetate, and washed with water, brine and dried over sodium sulphate. After evaporation of the solvent, the crude compound was subjected to reduction with a suitable reducing agent under suitable conditions, for example LiAlH$_4$ at 0° C. under N$_2$ atmosphere (30 min). The reaction was quenched by dropwise addition of ice-water and sodium sulphate. The reaction mixture was further diluted with solvent and filtered. The filtrate was concentrated in vacuo and the residue was purified using conventional procedures, typically column chromatography (silica gel, ethyl acetate, petroleum ether); to give the corresponding alcohol.

Salts of the compounds were formed using the general methodology described earlier.

Example 6

1-(2-(3-nitrophenyl)-2-hydroxy)ethyl-4-(3,5-bis(1,1-dimethylethyl)-4-hydroxyphenyl)methyl piperazine $^1$H NMR (CDCl$_3$) δ8.26 (s, 1H); 8.12 (dd, J=1.8 Hz and 8.2 Hz, 1H); 7.71 (d, J=7.7 Hz, 1H); 7.50 (t, J=8.0 Hz, 1H); 7.09 (s, 2H); 5.12 (s, 1H); 4.81 (dd, J=3.4 and 10.6 Hz, 1H); 3.46 (s, 2H); 2.60 (dd, J=3.4 and 12.4 Hz, 1H); 2.51 (bs, 8H); 2.42 (dd, J=10.7 and 12.4 Hz, 1H); 1.44 (s, 18H). MS (ESI) m/z 470 (M+1, 100).

Example 7

1-(2-(3-nitrophenyl)-2-hydroxy)ethyl-4-(3,5-bis(1,1-dimethylethyl)-4-hydroxyphenyl)methylpiperazine ditartrate M.p. 158–170° C. (dec). $^1$H NMR (d$_4$ MeOH) δ8.28, (s, 1H);); 8.14 (d, J=7.5 Hz, 1H); 7.72 (d, J=7.5 Hz, 1H); 7.54 (t, J=7.9 Hz, 1H); 7.25 (s, 2H); 7.20 (s, 1H); 5.04 (m, 1H); 3.13 (bs, 8H); 2.81 (m, 2H); 1.45 (s, 9H). MS (ESI) m/z 470.2 (M+1, parent, 100).

Example 8

1-(2-(3,4-methylenedioxyphenyl)-2-hydroxy)ethyl-4-(3,5-bis(1,1-dimethylethyl)-4-hydroxyphenyl)methyl piperazine (Compound 211)

M.p. 165–170° C. (dec). $^1$H NMR (CDCl$_3$) δ7.08 (s, 2H); 6.89 (d, J=1.6 Hz, 1H); 6.80 (ddd, J=0.5, 1.6 and 8.0 Hz, 1H); 6.76 (dd, J=0.4 and 10.1 Hz, 1H); 5.93 (s, 2H); 5.11 (s, 1H); 4.63 (dd, J=3.8 and 10.1 Hz, 1H); 3.44 (s, 2H); 2.77 (bs, 2H); 2.5–2.4 (m, 8H); 1.44 (s, 18H). MS (ESI) m/z 469.2 (M+1, 100).

Example 9

1-(2-(3,4-methylenedioxyphenyl)-2-hydroxy)ethyl-4-(3,5-bis(1,1-dimethylethyl)-4-hydroxyphenyl) methyl piperazine ditartrate m.p. 124–126° C. $^1$H NMR (DMSO-d$_6$) δ7.08 (s, 2H); 6.90 (s, 1H); 6.83 (m, 2H); 5.97 (d, J=1.1 Hz, 2H); 4.72 (dd, J=3.7 and 8.0 Hz, 1H); 4.16 (s, 4H); 3.62 (bs, 1H); 3.40 (bs, 1H); 2.80 (bs, 3H); 2.74 (bs, 5H); 1.37 (s, 9H). MS (ESI) m/z 469.2 (M+1, parent, 100).

Example 10

1-(2-(2-chlorothiophen-5-yl)-2-hydroxy)ethyl-4-(3,5-bis(1,1-dimethylethyl)-4-hydroxyphenyl) methylpiperazine (Compound 229)

M.p. 122–124° C. $^1$H NMR (CDCl$_3$) δ7.08 (s, 2H); 6.75 (d, J=3.8 Hz, 1H); 6.72 (dd, J=0.8 and 3.8 Hz, 1H); 5.11 (bs, 1H); 4.85 (dd, J=4.1 and 9.4 Hz, 1H); 3.45 (bs, 2H); 2.8–2.4 (m, 10H); 1.44 (s, 18H). MS (ESI) m/z 465.2 (M+1, 100).

Example 11

1-(2-(2-chlorothiophen-5-yl)-2-hydroxy)ethyl-4-(3,5-bis(1,1-dimethylethyl)-4-hydroxyphenyl)methyl piperazine ditartrate M.p. 155–160° C. (dec). $^1$H NMR (DMSO-d$_6$) δ7.11 (s, 2H); 6.93 (d, J=3.8 Hz, 1H); 6.83 (d, J=3.8 Hz, 1H); 4.85 (t, J=6.1 Hz, 1H); 4.18 (s, 4H); 3.68 (bs, 2H); 2.7–2.5 (m, 10H); 1.38 (s, 18H). MS (ESI) m/z 465.2 (M+1, parent, 100).

Example 12

1-(2-(3-chlorophenyl)-2-hydroxy)ethyl-4-(3,5-bis(1,1-dimethylethyl)-4-hydroxyphenyl)methylpiperazine M.p. (ditartrate) 165–166° C. $^1$H NMR (CDCl$_3$) δ7.39 (s, 1H); 7.26–7.23 (m, 3H); 7.08 (s, 2H); 5.14 (s, 1H); 4.69 (dd, J=3.4 and 10.5 Hz, 1H); 3.45 (s, 2H); 2.80–2.65 (m, 2H); 2.60–2.37 (m, 8H); 1.45 (s, 18H).

Example 13

1-(2-(4-pyridyl)-2-hydroxy)ethyl-4-bis(1,1-dimethylethyl)-4-hydroxyphenyl)methylpiperazine (Compound 238)

M.p. (ditartrate) 100–101° C. (dec). $^1$H NMR (CDCl$_3$) δ8.54, (d, J=6 Hz, 2H); 7.29 (d, J=6 Hz, 2H); 7.08 (s, 2H); 5.17 (s,1H); 4.7 (dd, J=3.4 and 10.6 Hz, 1H); 3.45 (s, 2H); 2.80–2.69 (m, 2H); 2.61–2.3 (m, 8H); 1.44 (s, 18H).

Example 14

1-(2-(4-fluorophenyl)-2-hydroxy)ethyl-4-(3,5-bis(1,1-dimethylethyl)-4-hydroxyphenyl)methylpiperazine (Compound 161)

M.p. (ditartrate) 168–169° C. NMR (CDCl$_3$, 300 MHz) δ7.32 (dd, J=8.7, 5.4 Hz, 2H); 7.11 (s, 2H); 7.01 (t, J=8.7 Hz, 2H); 5.17 (s, 1H); 4.72 (dd, J=10.2, 3.6 Hz, 1H); 3.51 (s, 2H); 2.86–2.62 (m, 2H); 2.58–2.45 (m, 8H); 1.44 (s, 18H).

Example 15

1-(2-(2,5-dimethoxyphenyl)-2-hydroxy)ethyl-4-(3,5-bis(1,1-dimethylethyl)-4-hydroxyphenyl) methylpiperazine (Compound 247)

M.p. (ditartrate) 171–172° C. NMR (CDCl$_3$, 200 MHz) δ7.17 (s, 1H); 7.14 (s, 2H); 6.79 (br s, 2H); 5.25 (s,1H); 5.17 (dd, J=10.0, 2.7 Hz, $_1$H); 3.8 (s, 3H); 3.79 (s, 3H); 3.63 (s, 2H); 3.10–2.65 (m, 9H); 2.54 (dd, J=12.5, 10 Hz, 1H); 1.47 (s, 18H.

Example 16

1-(2-(4-trifluoromethoxyphenyl)-2-hydroxy)ethyl-4-(3,5-bis(1,1-dimethylethyl)-4-hydroxyphenyl) methylpiperazine (Compound 193)

M.p. (ditartrate) 164–165° C. NMR (CDCl$_3$, 200 MHz) δ7.39 (d, J=8.7 Hz, 2H); 7.18 (d, J=8.7 Hz, 2H); 7.11 (s, 2H); 5.21 (s, 1H); 4.75 (dd, J=10.0, 3.8 Hz, 1H); 3.57 (s, 2H); 3.0–2.35 (m, 10H); 1.44 (s, 18H).

Example 17

1-(2-(4-chlorophenyl)-2-hydroxy)ethyl-4-(3-(1,1-dimethylethyl)-4-hydroxy-5-methylphenyl) methylpiperazine (Compound 265)

Step A: 1-(3-(1,1-dimethylethyl)-4-hydroxy-5-methylphenyl)methylpiperazine

This was prepared using the general methodology described for the preparation of 1-(3,5-bis(1,1-dimethylethyl)-4-hydroxyphenyl)methylpiperazine except that 3-(1,1-dimethylethyl)-4-hydroxy-5-methylbenzaldehyde replaced the 3,5-bis(1,1-dimethylethyl)-4-hydroxybenzaldehyde.

M.p. 155–160 ° C $^1$H NMR (CDCl$_3$) δ7.02 (d, J=2.0 Hz, 1H); 6.94 (d, J=1.5 Hz, 1H); 3.40 (s, 2H); 2.93 (t, J=4.9 Hz, 4H); 2.45 (bs, 4H); 2.23 (s, 3H); 1.41 (s, 9H).

Step B

This was prepared using the general methodology described previously except that 1-(3-(1,1-dimethylethyl)-4-hydroxy-5-methylphenyl)methylpiperazine was used instead of 1-(3,5-bis-(1,1-dimethylethyl)-4-hydroxyphenyl) methylpiperazine.

M.p. (dihydrochloride) 160–165° C. $^1$H NMR (d$_4$MeOH) δ7.43 (d, J=8.6 Hz, 2H); 7.38 (d, J=8.6 Hz, 2H); 7.25 (d, J=1.9 Hz, 1H); 7.14 (d, J=1.0 Hz, 1H); 5.07 (m, 1H); 4.25 (s, 2H); 3.8–3.1 (m, overlapping MeOH, 10H); 2.25 (s, 3H); 1.42 (s, 9H). MS (ESI); m/e 417.2 (M+1, parent, 100).

Example 18

1-(2-(4-hydroxyphenyl)-2-hydroxy)ethyl-4-(4-hydroxy-3,5-dimethylphenyl)methylpiperazine (Compound 271)

Step A: 1-(4-hydroxy-3,5-dimethylphenyl)methylpiperazine

This was prepared using the general methodology described for the preparation of 1-(3,5-bis(1,1-dimethylethyl)-4-hydroxyphenyl)methylpiperazine except that 4-hydroxy-3,5-dimethylbenzaldehyde replaced the 3,5-bis(1,1-dimethylethyl)-4-hydroxybenzaldehyde.

Step B

This was prepared using the general methodology described previously except that 1-(3-(1,1-dimethylethyl)-4-hydroxy-5-methylphenyl)methylpiperazine was used instead of 1-(3,5-bis-(1,1-dimethylethyl)-4-hydroxyphenyl) methylpiperazine.

M.p. (dihydrochloride) 158–160° C. $^1$H NMR (CDCl$_3$) δ7.15 (d, J=8.5 Hz, 2H); 6.89 (s, 2H); 6.68 (d, J=8.5 Hz, 2H); 5.29 (s, 1H); 4.63 (dd, J=8.7, 5 Hz, 1H); 3.43 (d, J=16 Hz, 1H); 3.33 (d, J=16 Hz, 1H); 2.8–2.44 (m, 10H); 2.18 (s, 6H).

Example 19

1-[3,4-dihydro-6-hydroxy-2,5,7,8-tetramethyl-2H-1-benzopyran-2-yl)methyl]-4-[2-(4-chlorophenyl)-2-hydroxyethyl]-piperazine (Compound 49)

4'-chloro-2-(piperazin-1-yl)propiophenone and 6-hydroxy-2,5,6,8-tetramethylchroman-2-carboxylic acid were coupled using 1,3-dicyclohexylcarbodiimide under standard conditions. The resulting oxo amide was reduced using LiAlH$_4$ in tetrahydrofuran in the presence of AlCl$_3$ (~0.3 eq)under similar conditions to those described previously for other reductions to afford the target compound.

M.p. (ditartrate) 88–90° C. $^1$H NMR (CDCl$_3$, 300 MHz) δ7.35 (s, 4H); 4.77–4.71 (m, 1H); 2.9–2.4 (m, 10H); 2.53 (s, 4H); 2.16 (s, 3H); 2.11 (s, 3H); 2.08 (s, 3H); 2.05–1.9 (m, 1H); 1.8–1.65 (m, 1H); 1.23 (s, 3H).

Example 20

1-[5-amino-2,4,6,7-tetramethyl-2,3-dihydrobenzofuran-2-yl methyl]-4-[2-(4-chlorophenyl)-2-hydroxyethyl]-piperazine (Compound 268)

(5-amino-2,4,6,7-tetramethyl-2-3-dihydrobenzofuranyl) methyl piperazine, which is prepared using the general procedure described in EP 0 483 772, was coupled with 2-bromo-4'-chloroacetophenone and the resultant oxo compound reduced, using conditions described previously, to afford the desired target compound as a mixture of diastereomers. $^1$H NMR (CDCl$_3$) δ7.31 (s, 2H), 7.29 (d, J=1.1 Hz, 2H), 4.70 (m, 1H), 3.10 (d, J=15.1 Hz, 1H), 2.9–2.3 (m, 13H), 2.1–2.0 (m, 9H), 1.4 (m, 3H).

Example 21

1-(2-(4'-chlorophenyl)-2-hydroxy)ethyl-4-(2-(2', 3', 5'-trimethyl-4'-hydroxyphenoxy))ethyl piperazine Step A 4-acetoxy-2,3,5-trimethyl-1-(2-bromoethoxy) benzene A mixture of 4-acetoxy-2,3,5-trimethyl phenol (0.94 g, 4.82 mmol), dibromoethane (4 mL), potassium carbonate (0.80 g, 1.2 eq), 18-crown-6 (20 mg) in acetonitrile (15 mL) was stirred and heated at reflux under an atmsophere of N$_2$ for 8 days. After this time the mixture was concentrated at reduced pressure and the residue partitioned between CH$_2$Cl$_2$ and 1M HCl. The organic phase was dried, filtered and concentrated at reduced pressure. The residue was purified by flash chromatography (9:1 ethyl acetate, petroleum spirit). The product was obtained as a white solid (34%) and was recrystallised from petroleum spirit as colourless needles, m.p 59–60° C. $^1$H NMR (CDCl$_3$) δ6.55 (s, 1H), 4.24 (t, J=6.2 Hz, 2H), 3.64 (t, J=6.2 Hz, 2H), 2.32 (s, 3H), 2.16 (s, 3H), 2.11 (s, 3H), 2.05 (s, 3H).

Step B 1-t-Butylcarbonyloxy-4-(2-(2', 3', 5'-trimethyl-4'-acetoxyphenoxy))ethyl piperazine A mixture of 4-acetoxy-2,3,5-trimethyl-1-(2-bromoethoxy)benzene (592 mg, 1.97 mmol), t-butylcarbonyloxypiperazine hydrochloride (1.5 g, 3.5 eq), triethylamine (1.2 mL, 4.5 eq) in acetonitrile was heated at reflux under an atmosphere of N$_2$ for 24 hours. After this time the mixture was partitioned between CH$_2$Cl$_2$ and water. The organic phase was dried, filtered and concentrated at reduced pressure and the residue purified by flash chromatography, (1:1, ethyl acetate, petroleum spirit).

The product was obtained as an off-white solid (75%) which was recrystallised from petroleum spirit as fine needles, m.p. 62–64° C. $^1$H NMR (CDCl$_3$) δ6.56 (s, 1H), 4.09 (bs, 2H), 3.47 (bs, 4H), 2.86 (bs, 2H), 2.57 (bs, 4H), 2.32 (s, 3H), 2.12 (s, 3H), 2.11 (s, 3H), 2.04 (s, 3H), 1.46 (s, 9H).

Step C 1-(2-(2',3',5'-trimethyl-4'-acetoxyphenoxy))ethyl piperazine

A solution of 1-t-butylcarbonyloxy-4-(2-(2',3',5'-trimethyl)4'-acetoxyphenoxy)ethyl piperazine (322 mg, 0.793 mmol), in dichloromethane (6 mL) was treated with trifluoroacetic acid (2 mL). The solution was stirred at room temperature for 30 minutes and then carefully poured into saturated sodim bicarbonate solution. The mixture was extracted with CH$_2$Cl$_2$. The organic extracts were dried, filtered and concentrated at reduced pressure to afford the product as a colourless oil (98%). $^1$H NMR (CDCl$_3$) d 6.56 (s, 1H), 4.06 (t, J=5.7 Hz, 2H), 3.95 (bt, 4H), 2.81 (t, J=5.7 Hz, 2H), 2.60 (bt, 4H), 2.32 (s, 3H), 2.12 (s, 3H), 2.11 (s, 3H), 2.04 (s, 3H).

Step D 1-(2-(4'-chlorophenyl)-2-hydroxy)ethyl-4(2-(2',3',5'-trimethyl-4'-acetoxyphenoxy))ethyl piperazine This was prepared using the general methodology described previously except that 1-(2-(2',3',5'-trimethyl)-4'-acetoxyphenoxy)ethyl piperazine was used instead of 1-(3, 5-bis-(1,1-dimethylethyl)-4-hydroxyphenyl)methyl piperazine.

$^1$H NMR (CDCl$_3$) d 7.31 (s, 4H), 6.56 (s, 1H), 4.70 (dd, J=3.5 Hz and 10.5 Hz, 1H), 4.07 (t, J=5.7 Hz, 2H), 2.84 (t, 5.7 Hz, 2H), 2.8–2.5 (m, 8H), 2.52 (dd, J=3.6 and 12.5 Hz, 1H), 2.41 (dd, J=10.5 Hz and J12.5 Hz, 1H), 2.32 (s, 3H), 2.13 (s, 3H), 2.11 (s, 3H), 2.04 (s, 3H).

Step E 1-(2-(4'-chlorophenyl)-2-hydroxy)ethyl-4-(2-(2',3',5'-trimethyl-4'-hydroxyphenoxy))ethyl piperazine A solution of 1-(2-(4'-chlorophenyl)-2-hydroxy)ethyl4-(2-(2',3',5'-trimethyl-4'-acetoxyphenoxy))ethyl piperazine in methanol was treated with 2M aqueous NaOH. The mixture was stirred at room temperature for 30 mins. The mixture was then made neutral by addition of 1M HCl and then extracted wtih CH$_2$Cl$_2$. The organic extract was dried, filtered and concentrated at reduced pressure. The residue was purified by flash chromatography to give the product as a colourless solid, m.p.148–150° C.

$^1$H NMR (CDCl$_3$) d 7.31 (s, 4H), 4.71 (dd, J=3.5 Hz and 10.6 Hz, 1H), 4.04 (t, J=5.7 Hz, 2H), 2.9–2.5 (m, 10H), 2.52 (dd, J=3.5 Hz and 12.5 Hz, 1H), 2.43 (dd, J=10.6 Hz and 12.5 Hz, 1H), 2.22 (s, 3H), 2.17 (s, 3H), 2.14 (s, 3H).

Example 22

(R,R)-racemic-1-(3-(4-Hydroxyphenyl)-3-hydroxy) propyl-4-(3,5-bis(1,1-dimethylethyl)-4-hydroxyphenyl)methylpiperazine (Compound 2)

The title compound was prepared from commercially available 4'-hydroxypropiophenone which was brominated under standard conditions and reacted according to the general methodology described for example 6–16.

The resulting diastereomeric mixture was separated into the syn ((R,R) racemic) and anti ((R,S) racemic) diastereoisomers on silca gel. One as Example 22 the other as Example 23.

M.p. (ditartrate) 125–127° C. NMR (CDCl$_3$+1 drop d$_4$ MeOH 300 MHz) δ7.05 (d, J=8.4 Hz, 2H); 7.02 (s, 2H); 6.68 (d, J=8.4 Hz, 2H); 4.07 (d, J=9.7 Hz, 1H); 3.43, (br s, 2H); 2.71–2.4 (m, 9H); 1.35 (s, 18H); 0.66 (d, J=7.3 Hz, 3H).

Example 23

(R,S)-racemic-1-(3-(4-Hydroxyphenyl)-3-hydroxy)
propyl4-(3,5-bis(1,1-dimethylethyl)-4-
hydroxyphenyl)methylpiperazine (Compound 2)

See Example 22.

M.p. (ditartrate) 129–130° C. NMR (CDCl$_3$, 200 MHz) δ7.08 (s, 2H); 7.06 (d, J=8.5 Hz, 2H); 6.63 (d, J=8.5 Hz, 2H); 5.16 (s, 1H); 4.84 (d, J=3.1 Hz, 1H); 3.48, (s, 2H); 2.8–2.4 (m, 9H); 1.38 (s, 18H); 0.82 (d, J=6.8 Hz, 3H).

Example 24

(+) and (−) enantiomers of 1-(2-(4-Chlorophenyl)-
2-hydroxy)ethyl-4-(3,5-bis(1,1-dimethylethyl)-4-
hydroxyphenyl)methylpiperazine ((+) and (−)
enantiomers of Compound 33)

The racemic compound of Example 3 (compound 33) has been resolved into its optical isomers by conversion to S-cyhalothrin esters (Mathews et al., 1988). The diastereomeric esters were separated using column chromatography (silica gel, 0.2:1, Ethyl acetate, petroleum ether). The two diastereomers are subjected to LiAlH$_4$ reduction under standard conditions to give the enantiomers of Compound 33.

(+)-1-(2-(4-Chlorophenyl)-2-hydroxy)ethyl-4-(3,5-
bis(1,1-dimethylethyl)-4-hydroxyphenyl)
methylpiperazine

[α]$_D$=42.1 (c.1, CHCl$_3$);M.p. (Ditartrate) 174–175° C.

(−)-1-(2-(4-Chlorophenyl)-2-hydroxy)ethyl-4-(3,5-
bis(1,1-dimethylethyl)-4-hydroxyphenyl)
methylpiperazine

[α]$_D$=−42.1 (c.1, CHCl$_3$); M.p. (ditartrate) 172–174° C.

Example 25

1-(2-(4-Chlorophenyl)-2-hydroxy)ethyl-4-[(3,5-bis
(1,1-dimethylethyl)-4-hydroxyphenyl)-1-oxoprop-2-
en-1-yl]piperazine (Compound 45)

The title compound was prepared using the general methodologies previously described and 1-(3,5-bis(1,1-dimethylethyl)-4-hydroxyphenyl propenoic acid which was prepared according to the procedure of WO 95/15958.

$^1$H NMR (CDCl$_3$, 300 Mhz) δ7.65 (d,J=15.3 Hz, 1H); 7.35 (s, 2H);7.32(s, 4H); 7.32(s, 4H); 6.67 (d,J=15.3 Hz, 1H); 5.47 (s, 1H); 4.76 (dd, J=9.5, 4.4 Hz, 1H); 3.88, (br s, 1H); 3.85–3.67 (m, 4H); 2.84–2.74 (m, 2H); 2.57–2.41 (m, 4H); 1.46 (s, 18H).

Biological Activity

For convenience the results tabulated below refer to the compounds tested as the free base, however compounds may have been tested either as the free base or as a salt, typically salts used were the ditartrate or hydrochloride.

NMDA Assay Procedure

The NMDA receptor-ionophore complex consists of a number of interacting domains, including one for polyamines where ifenprodil binds to exert its non-competitive antagonism. Competitive binding of the compounds of the invention against iodinated ifenprodil was determined in rat cortical membrane as described elsewhere (Beart et al., 1991).

Membranes were prepared from freshly dissected brains of adult male Sprague-Dawley rats (175–250 g). Ifenprodil was iodinated with 1 mCi of Na$^{125}$I in the presence of chloramine-T (25 nmoles). The reaction was terminated by addition of sodium metabisulfite and the $^{125}$I-labelled ifenprodil was extracted with ethyl acetate from remaining Na$^{125}$I. The ethyl acetate extract was further purified by descending paper chromatography in ammonium formate buffer (0.1M, pH 8.5) in which the $^{125}$I-ifenprodil migrated with Rf~0.15. The purified material was stored in methanol at −20° C.

Briefly, assays were performed in 5 mM Tris HCl pH 7.7 containing [$^{125}$I]ifenprodil (20,000 dpms, ~20 pM) and cortical membranes (0.5 mg wet wt.) in a final volume of 0.5 mL. Incubations were for 30 min. at 20° C., in triplicate, employing 12 concentrations of competing drugs. Non-specific binding was defined with 10 mM spermine. Assays were terminated by rapid filtration through GF/B filter paper and washing.

Binding data were analysed by the iterative curve fitting programs EBDA and LIGAND as full described elsewhere (Beart et al., 1989)

The Ki of some of the compounds of the present invention is shown in Table 2

TABLE 2

| Compound | ki ($\mu$M) |
| --- | --- |
| 1 | 13.0 ± 0.6 |
| 33 | 10.8 ± 0.6 |
| 34 | 14.6 ± 2.8 |
| 35 | 16.8 ± 3.2 |
| 49 | 15.2 ± 3.9 |
| 65 | 7.0 ± 1.5 |
| 161 | 5.4 ± 0.6 |
| 193 | 11.7 ± 1.0 |
| 211 | 19.1 ± 5.7 |
| 229 | 19.6 ± 5.2 |
| 247 | 8.5 ± 3.1 |
| 2 ((R, R)-racemic) | 15.7 ± 4.6 |
| 2 ((R, S)-racemic) | 14.5 ± 5.6 |
| 265 | 13.2 ± 2.6 |
| Example 6 | 15.1 ± 6.1 |
| Example 21 | 6.1 ± 2.0 |
| ifenprodil | 19.5 ± 1.2 |

Antioxidant Assay

Malondialdehyde (MDA) is one of the breakdown products of lipid peroxidation. MDA reacts with thiobarbituric acid (TBA) to produce a characteristic pink colour that can be measured spectrophotomerically. Measuring the capacity of compounds to inhibit this colour formation and hence the formation of thiobarbituric acid reactive substances (TBARs) has proved a useful test for antioxidant compounds. The present method has been modified from those described by Ohkawa et al. (1979) and Cheng et al. (1994).

Briefly, rat brain 10% homogenates were prepared in aqueous 20 mM Tris-HCl buffer, pH 7.4 media using a Polytron homogeniser. Assays contained 100 μl of rat brain homogenate and various concentrations of test compound (10 μl) were incubated for 10 min at 37° C. Ten μl of 1.0 or 0.1 mM Fe$^{3+}$ solution was then added to stimulate lipid peroxidation and the homogenates were incubated for a further 30 min at 37° C. The reaction was stopped by addition of sodium dodecyl sulphate (100 μl of 8.1% wt/vol solution) and 750 μl of 20% sodium acetate buffer (pH 3.5). The precipitated proteins were then removed by centrifugation at 10000 g for 15 min. Five hundred μl of clear supernatant was heated with 1 ml TBA solution (0.8% wt/vol) at 95° C. for 60 min. The samples were cooled and 200 μl of each sample was pipetted into a 96 well plate and absorbencies read at 532 nm using a Ceres UV900C microplate reader. Blank values representing samples containing 20 mM Tris-HCl and $Fe^{3+}$ only were subtracted from all values. Each value was expressed as a percentage of that for samples containing homogenate and $Fe^{3+}$ only (ie, no drug). From concentration response curves the concentrations causing 50% inhibition of MDA formation ($IC_{50}$ values) for the test compounds were determined by computer-assisted linear regression analysis according to published methods (Leutner, 1982). These compared favourably with the values obtained in the assay with the benchmark antioxidant compound trolox.

The $\sim IC_{50}$ values of the compounds of the present invention are shown Table 3

TABLE 3

| Compound | $\sim IC_{50}$ ($\mu$M) | |
|---|---|---|
| | $Fe^{3+}$ 100 $\mu$M | $Fe^{3+}$ 1000 $\mu$M |
| 1 | 32.7 | 18.3 |
| 33 | 57.2 | 41.4 |
| 34 | 25.4 | 36.3 |
| 35 | 27.9 | 9.3 |
| 49 | 3.6 | 2.4 |
| 65 | 96.8 | 53.3 |
| 161 | 19.5 | 15.2 |
| 193 | 59.6 | 22.3 |
| 247 | 9.9 | 10.3 |
| 2 ((R, R)-racemic) | 16.8 | 14.9 |
| 2 ((R, S)-racemic) | 23.8 | 24.1 |
| 265 | 59.4 | 38.5 |
| trolox | 88.2 | 90.8 |
| example 6 | 32.4 | 26.6 |
| example 21 | <3 | <1 |

Although the classical determination of MDA by the thiobarbituric-acid method is widely used, some laboratories have reported difficulties in establishing a reliable assay (Esterbauer et al, 1990) and therefore the Sapphire LPO-586 colorimetric assay of lipid peroxidation was additionally employed (Melchiorri et al, 1995).

The procedures outlined in the Sapphire LPO-586 kit were carried out with the following modifications. Briefly rat brain 10% homogenates were prepared in aqueous 20 mM Tris-HCl buffer, pH 7.4 media using a Polytron homogeniser. Assays contained 100 $\mu$l of rat brain homogenate and various concentrations of test compound (10 $\mu$l) were incubated for 10 min at 37° C. Therefore, 10 $\mu$l of 0.1 mM $Fe^{3+}$ solution was then added to stimulate lipid peroxidation and the homogenates were incubated for a further 30 min at 37° C. Chromogenic reagent (1-methyl-2-phenylindole, 325 $\mu$l) at the concentration of 10.3 mM in acetonitrile was added and the reaction was started by the addition of 75 $\mu$l of 37% aqueous HCl to each tube. The reaction mixture was incubated for 60 min at 45° C., cooled on ice, centrifuged at 5000 g for 7 min and 200 $\mu$l of each sample was pipetted into a 96-well plate and absorbances read at 586 nm using a Ceres UV900C microplate reader. Following subtraction of blank values, analysis was performed as for the TBARS assay.

Sodium Channel Binding Assay

The general procedure of Catterall et al. (1981) was used with minor modifications. Generally, washed rat brain homogenates (350 $\mu$L of a 25 mg/mL membrane preparation) were incubated with [$^3$H]-batrachotoxinin A 20-$\alpha$-benzoate (final assay concentration up to 1.5 nM) and scorpion toxin (from Leiurus quinquestriatus [Sigma Catalogue No. V5251]) (final assay concentration up to 40 $\mu$g/mL) with and without the test compound over a concentration range of $10^{-8}$ to $10^{-4}$ M in HEPES buffer (50 mM HEPES dissolved in 50 mM Tris HCl pH 7.4 and containing 130 mM choline chloride, 5.4 mM KCl, 0.8 mM MgSO4, 5.5 mM glucose) in a final volume of 500 $\mu$L. Non-specific binding was defined using a saturating concentration of veratridine (0.1 mM) and a range of concentrations of [$^3$H]-batrachotoxinin A 20-$\alpha$-benzoate. The assay tubes are incubated for 30 minutes at 37° C. before termination by rapid filtration through GF/B filter paper and washing using a cell harvester. Bound radioactivity is assessed using a scintillation counter. From dose response curves approximate $IC_{50}$ and Ki values for the test compounds were determined.

The $IC_{50}$ and Ki of some of the compounds of the present invention is shown in Table 4.

TABLE 4

| Compound | $IC_{50}$ ($\mu$M) | Ki ($\mu$M) |
|---|---|---|
| 33 | 0.28 ± 0.1 | 0.64 ± 0.1 |

Assay for NMDA-induced Toxicity in Neuronal Cultures

Neuronal cell death was assessed using a 3-(4,5-dimethylthiazol-2yl)-2,5-diphenyltetrazolium bromide (MTT) assay in which NMDA-induced cellular changes are reflected as altered mitochondrial activity (Ankarcrona et al., 1995), as estimated by the formation of a formazan dye, which is measured spectrophotometrically. The procedure employed is essentially that of Roehm et al. (1991) with minor modifications as previously described elsewhere in work from our laboratories Larm et al. (1996).

Primary cultures of murine neocortical neurones were established as described elsewhere (Larm et al., 1996). The effects of experimental compounds were tested in the cultures at 8 days in vitro. Exposure to NMDA (600 $\mu$M, 1 h) and other compounds was performed in an humidified incubator (5% $CO_2$, 8% $O_2$) at 37° C. in anti-oxidant free medium with compounds under evaluation being added 30 min prior to NMDA. For these conditions the culture medium was modified by omitting the following components: D,L-$\alpha$-tocopherol, D,L-$\alpha$-tocopherol acetate, catalase, superoxide dismutase and L-glutamine. Other details are described in Larm et al. (1996). Absorbance was read at 570 nm using a Ceres UV900 microplate reader. Control cultures were included in each experiment containing either vehicle alone or vehicle plus compound. These controls were taken as 100% neuronal viability, under the experimental conditions, and each experiment also included 500 $\mu$M L-glutamate representing 100% glutamatergic neuronal cell death. Background cell death in vehicle control cultures was 5–8%.

Concentration-response curves were generated as described elsewhere (Larm et al., 1996). The $ED_{50}$ for inhibition of NMDA-induced toxicity by some compounds of the present invention is shown in Table 5.

TABLE 5

| Compound | $EC_{50}$ ($\mu$M) |
|---|---|
| 33 | 0.39 |
| 49 | 2.9 |
| 65 | 0.24 |
| Example 12 | 0.76 |
| 2((R, R)-racemic) | 1.28 |
| 2((R, S)-racemic) | 3.01 |

Throughout this specification, unless the context requires otherwise, the word "comprise", or variation such as "comprises" or "comprising" will be understood to imply the inclusion of a stated integer or group of integers but not the exclusion of any other integer or group of integers.

Those skilled in the art will appreciate that the invention described herein is susceptible to variations and modifications other than those specifically described. It is to be understood that the invention includes all such variations and modifications which fall within its spirit and scope. The invention also includes all the steps, features, compositions and compounds referred to or indicated in this specification, individually or collectively, and any and all combinations of any two or more of said or features.

References

Abbott, F. V. et al., *Pain,* 60, 91–102 (1995)
Ankarcrona M. et al., *Neuron,* 15, 961–973 (1995)
Beart, P. M. et al., *Br. J. Pharmacol.,* 114, 1359–1364 (1995)
Beart, P. M. et al., *J. Neurochem.,* 53, 779–788 (1989).
Beart, P. M. et al., *Neurosci. Lett.,* 124, 187–189 (1991).
Beart, P. M. et al., *Mol. Neuropharmacol.,* 2, 113–119 (1992)
Bonfoco, E. et al., *Proc. Natl. Acad. Sci. USA.,* 92, 7162–7166 (1995)
Brown, C. M., et al., *Br. J. Pharmacol.,* 115, 1425–1432 (1995)
Catterall, W. A. et al., *J. Biol. Chem.,* 256, 8922–8927 (1981)
Carter, C. J. et al., *Eur. J. Pharmacol.,* 164, 611–612 (1989)
Carter, C. J. et al., *J. Pharmacol. Exp. Ther.,* 253, 475–482 (1990)
Cheng et al., *J. Neurochem.,* 63, 895–902 (1994)
Choi, D. W. et al., *J. Neurobiol.,* 23, 1261–1276 (1992)
Esterbauer, H. et al., *Meth. Enzymol,* 186, 407–421 (1990)
Gotti, B. et al., *J. Pharmacol. Exp. Ther.,* 247, 1211–1221 (1988)
Greene, T. W. (1991) Protective Groups in Organic Synthesis, John Wiley and Sons, Inc.
Jacobsen, E. J. et al., *J. Med. Chem.,* 35, 4464–4472 (1992)
Larm, J. A. et al., *Eur. J. Pharmacol.,* 314, 249–254 (1996)
Leutner, C (1982) Documenta Geigy Scientific Tables. 8th Ed., Ciba Geigy, Basel, pp 210–215.
Lipton, S. A. et al., *N. Engl. J. Med.,* 330, 613–622 (1994)
Lysko, P. G. et al., *Stroke,* 25, 2476–82 (1995)
Mathews, B. M. et al., *Aust. J. Chem,* 41, 1697–1709 (1988)
Melchiorri, D., et al, *FASEB J.,* 9, 1205–1210 (1995)
Meldrum, B. et al., *Trends Pharmacol. Sci.,* 11, 379–387 (1990)
Mercer, L. D. et al., *J. Neurochem,* 61, 120–126 (1993)
Nicola, C. et al., *J. Neurochem,* 63, 2248–2258 (1994)
Ohkawa, H. et al., *Analytical Biochemistry.,* 95, 351–358 (1979)
Perti, O. N. et al., *Indian J. Chem.,* 5, 622–623 (1967)
Reynolds, I. J. et al., *Mol. Pharmacol.,* 36, 758–765 (1989)
Robinson, T. N. et al., *Mol. Neuropharmacol.,* 1, 31–35 (1990)
Roehm, N. W. et al., *Immuno. Methods,* 142, 257–(1991)
Sonsalla, P. K., et al., *J. Pharmacol. Exp. Ther.,* 256, p.506–12 (1991)
Standaert, D. G. et al., *Comp. Neurol.,* 343, 1–6 (1994)
Urenjak, J. et al., *Pharmacol. Rev.,* 48, 21–68 (1996)
Williams, K., *Mol. Pharmacol.,* 44, 851–859 (1993)

What is claimed is:
1. A compound of Formula (1)

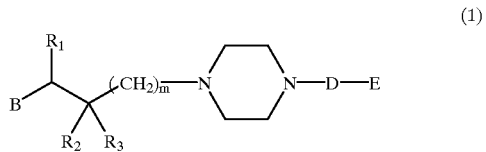

wherein

B is aryl which is unsubstituted or substituted with one or more substituents which are alkyl, alkenyl, alkynyl, aryl, fluoro. chloro, bromo, hydroxy, alkyloxy, alkenyloxy, aryloxy, acyloxy, amino, alkylamino, dialkylamino, arylamino, mercapto, alkylthio, arylthio, cyano, nitro, aryl, amido, alkylamido, dialkylamido, carboxyl, trifluoromethyl, trifluoromethoxy, or two substituents which, when taken together with the carbon atoms to which they are attached, form a 5- or 6-membered aromatic or non-aromatic ring containing 0, 1 or 2 heteroatoms selected from the group consisting of nitrogen, oxygen and sulfur;

$R^1$ is hydroxy;

$R^2$ and $R^3$ are the same or different and are independently selected from hydrogen or $C_{1-3}$ alkyl;

m is 0, 1 or 2;

D is straight chain or branched alkyl, oxoalkyl, alkenyl or oxoalkenyl, said D containing 1 to 6 carbon atoms;

E is

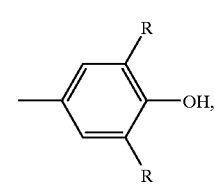

a

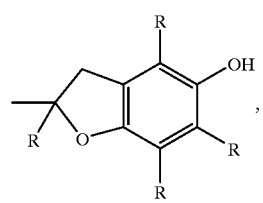

b

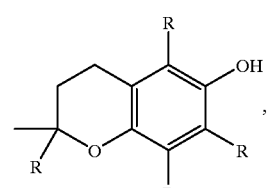

c

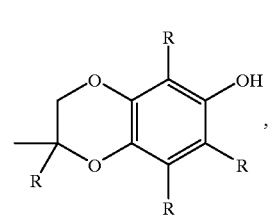

d

-continued

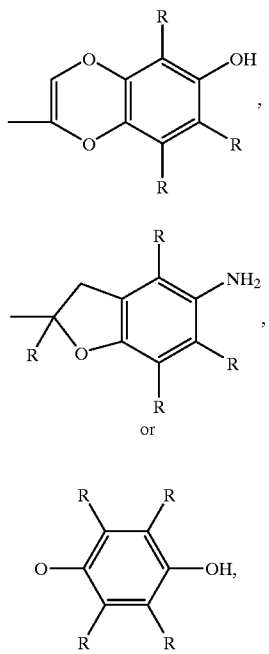

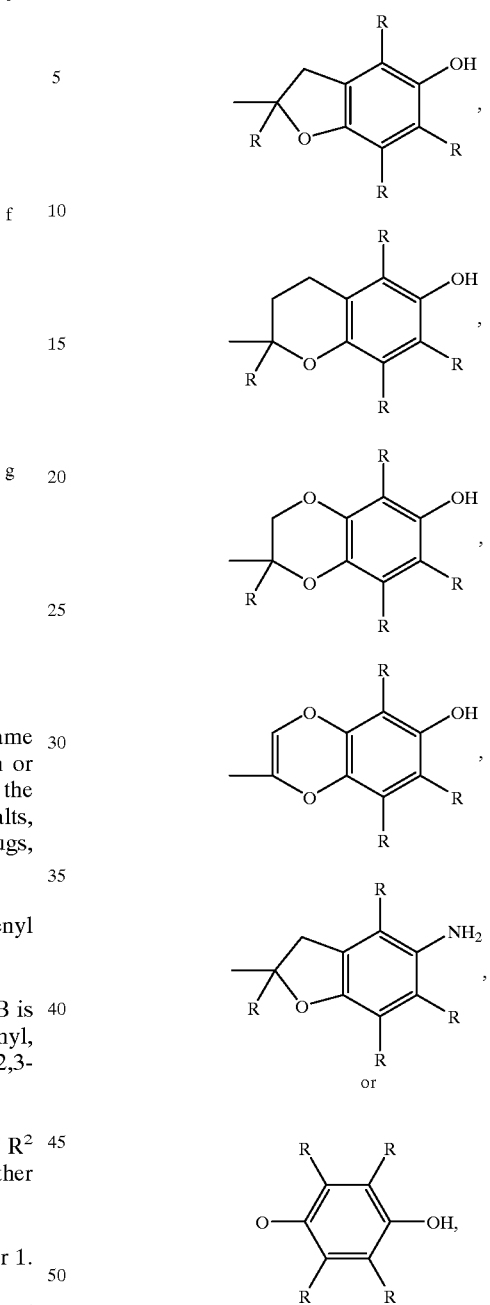

wherein for each group (a) to (g), each group R is the same or different and independently selected from hydrogen or alkyl, or a corresponding amino derivative wherein the phenolic hydroxy on E is replaced by amino, or salts, solvates, pharmaceutically acceptable derivatives, prodrugs, tautomers or isomers thereof.

2. A compound according to claim 1 wherein B is phenyl or optionally substituted phenyl.

3. A compound according to either claim 1 wherein B is selected from the group consisting of unsubstituted phenyl, phenyl optionally substituted in the para position or 2,3-dihydro-5-benzo[b]thienyl.

4. A compound according to claim 1 wherein one of $R^2$ and $R^3$ is selected from hydrogen or $C_{1-3}$ alkyl and the other is hydrogen.

5. A compound according to claim 1 wherein m is 0 or 1.

6. A compound according to claim 1 wherein D is selected from the group consisting of $(CH_2)_n$, $C(=O)(CH_2)_{n-1}$, $C(=O)CH=CH$, $(CH_2)_nCH=CH$, wherein n is from 1 to 6.

7. A compound according to claim 1 wherein E is selected from the group consisting of groups (a) to (g) wherein the groups (a) to (g) are as follows:

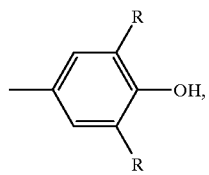

wherein for each group (a) to (g), each group R is the same or different and independently selected from hydrogen or alkyl.

8. A compound according to claim 7 wherein at least one of the R groups in respect of each of groups (a) to (g) is alkyl.

9. A compound according to claim 7 wherein at least two of the R groups in each of groups (a) to (g) are alkyl.

10. A compound according to claim 7 wherein E is selected from the group consisting of groups (a), (b), (c), (f) or (g).

11. A method of treating a subject suffering from head trauma, stroke, cardiac arrest, ischaemia, hypoxia, hypoglycaemia, epilepsy, lateral amyotrophic sclerosis and variants thereof, schizophrenia or atherosclerosis comprising administering thereto a therapeutically effective amount of a compound according to claim 1.

12. A method of treating a subject suffering from epilepsy, epileptic psychotic symptoms, or hypertension comprising administering thereto a therapeutically effective amount of a compound according to claim 1.

13. A method of providing pain relief or antinociception comprising administering to a subject in need thereof an effective amount to a compound according to claim 1.

14. A pharmaceutical composition comprising a therapeutically effective amount of a compound according to claim 1 or a pharmaceutically acceptable salt thereof together with one or more pharmaceutically acceptable carriers, diluents, adjuvants or excipients.

15. A method for the manufacture of a compound of formula (1)

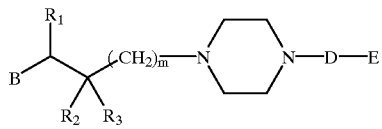

(1)

wherein B, $R^1$, $R^2$, $R^3$, m, D and E are as defined in claim 1, which comprises (a) reacting a compound of formula (3)

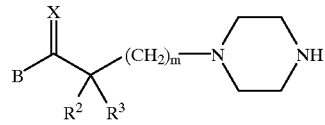

(3)

wherein B, $R^2$, $R_3$ and m are as defined above and X is $R^1$ as defined above and hydrogen, or oxygen with
(i) L—D—E wherein L is a leaving group and D and E are as defined above; or
(ii) the aldehyde OHC—F—E wherein E is as defined above and F is selected from the group consisting of $(CH_2)_{n-1}$ or $(CH_2)_{n-1}CH=CH$; or
(iii) the acid $HO_2C$—F—E wherein E and F are as defined above.

16. A method according to claim 15 wherein the compound of formula (3) is prepared by reacting the compound of formula (2)

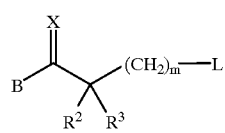

(2)

wherein B, X, $R^2$, $R^3$, m and L are as defined in claim 15 with the optionally protected piperazine

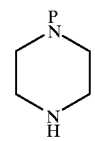

wherein P is hydrogen or a protecting group.

17. A method for the manufacture of a compound according to formula (1)

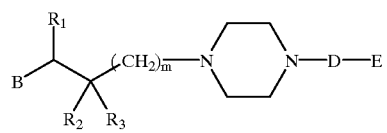

(1)

wherein B, $R^1$, $R^2$, $R^3$, m, D and E are as defined in claim 1; which comprises (a) reacting compound of formula (4)

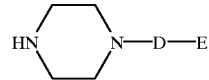

(4)

wherein D and E are as defined above; with
(b)

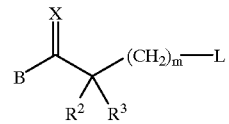

(2)

wherein B, $R^2$, $R^3$ and m are as defined above, X is $R^1$ as defined above and hydrogen, or oxygen and L is a leaving group.

18. A method according to claim 17 wherein the compound of formula (4) is prepared by reacting the optionally protected piperazine

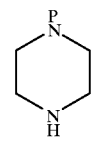

wherein P is hydrogen or a protecting group with
(i) L—D—E wherein L is a leaving group and D and E are as defined in claim 1; or
(ii) the aldehyde OHC—F—E wherein F is selected from the group consisting of $(CH_2)_{n-1}$ or $(CH_2)_{n-1}CH=CH$; or
(iii) the acid $HO_2C$—F—E wherein F and E are as defined above.

19. The compound according to claim 1 wherein B is phenyl or optionally substituted phenyl, R' is hydrogen, $R^2$ and $R^3$ are the same or different and are hydrogen or $C_{1-3}$ alkyl, D is $(CH_2)_n$, $C=O(CH_2)_{n-1}$, or $(CH_2)_n CH=CH$, m is 0, 1, or 2, and n is 1–6.

20. The compound according to claim 19 wherein B is unsubstituted phenyl or

21. The compound according to claim 19 wherein B is unsubstituted phenyl or para substituted phenyl.

22. The compound according to claim 19 wherein D is $(CH_2)_n$.

23. The compound according to claim 19 wherein E is a, b, c, f or g.

24. The compound according to claim 1 wherein

B is unsubstituted phenyl, phenyl substituted in the para position or 2,3-dihydro-5-benzo[b]thienyl;

$R_1$ is hydroxy;

one of $R_2$ and $R_3$ is hydrogen or $C_{1-3}$ and the other is hydrogen;

D is $(CH_2)_n$, or $(CH_2)_n$—CH=CH, m is 0 or 1, and n is 1–6.

25. The compound according to claim 24 wherein E is a, b, c, f or g.

26. The compound according to claim 24 wherein D is $(CH_2)_n$.

27. The compound according to claim 24 wherein

B is unsubstituted or substituted phenyl in the para position;

D is $(CH_2)_n$;

E is a, b, c, f or g.

28. The compound according to claim 1 which is 1-(2-(4-chlorophenyl)-2-hydroxy)ethyl-4-(3,5,bis(1,1-dimethylethyl)-4-hydroxyphenyl)methylpiperazine.

29. The compound according to claim 1 wherein the compound is 1-[3,4-dihydro-6-hydroxy-2,5,7,8-tetramethyl-2H-1-benzopyran-2-yl)methyl]-4-[2-(4-chlorophenyl)-2-hydroxyethyl]-piperazine.

* * * * *